US008895739B2

(12) United States Patent
Schafmeister et al.

(10) Patent No.: US 8,895,739 B2
(45) Date of Patent: Nov. 25, 2014

(54) ACYLATION OF HINDERED AMINES AND FUNCTIONALIZED BIS-PEPTIDES OBTAINED THEREBY

(75) Inventors: Christian E. Schafmeister, Merion Station, PA (US); Zachary Z. Brown, Green Bay, WI (US)

(73) Assignees: Temple University of the Commonwealth System of Higher Education, Philadelphia, PA (US); University of Pittsburgh of the Commonwealth System of Higher Education, Pittsburgh, PA (US)

( * ) Notice: Subject to any disclaimer, the term of this patent is extended or adjusted under 35 U.S.C. 154(b) by 178 days.

(21) Appl. No.: 13/006,912

(22) Filed: Jan. 14, 2011

(65) Prior Publication Data
US 2011/0184171 A1 Jul. 28, 2011

Related U.S. Application Data

(63) Continuation-in-part of application No. PCT/US2009/050635, filed on Jul. 15, 2009.

(60) Provisional application No. 61/080,861, filed on Jul. 15, 2008.

(51) Int. Cl.
| | | |
|---|---|---|
| C07D 241/52 | (2006.01) | |
| C07D 487/20 | (2006.01) | |
| C07K 5/062 | (2006.01) | |
| C07D 487/22 | (2006.01) | |
| C07D 519/00 | (2006.01) | |

(52) U.S. Cl.
CPC .......... *C07D 487/20* (2013.01); *C07K 5/06034* (2013.01); *C07D 487/22* (2013.01); *C07D 519/00* (2013.01)
USPC ...................................................... 544/349

(58) Field of Classification Search
USPC ...................................................... 544/349
See application file for complete search history.

(56) References Cited

U.S. PATENT DOCUMENTS

| | | | |
|---|---|---|---|
| 6,060,585 A | 5/2000 | Gellman et al. | |
| 2004/0077879 A1 | 4/2004 | Schafmeister | |
| 2004/0082783 A1 | 4/2004 | Schafmeister | |
| 2004/0106619 A1* | 6/2004 | Mitsuya et al. | 514/249 |
| 2005/0215557 A1* | 9/2005 | Habashita et al. | 514/249 |
| 2005/0267114 A1* | 12/2005 | Takaoka et al. | 514/249 |
| 2007/0155713 A1* | 7/2007 | Nishizawa et al. | 514/210.16 |

FOREIGN PATENT DOCUMENTS

| | | | |
|---|---|---|---|
| WO | WO 2004013282 | * | 7/2003 |
| WO | WO2004/013282 | | 2/2004 |

OTHER PUBLICATIONS

Schafmeister, et al., Chemistry—A European Journal (2008), 14(21), 6406-6412, received Dec. 8, 2007.*
Levins, et al., Organic Letters (2006), 8(13), 2807-2810.*
Pornsuwan, et al., Journal of the American Chemical Society (2006), 128(12), 3876-3877.*
Levins (II), et al., Journal of Organic Chemistry (2005), 70(22), 9002-9008.*
Levins (III), et al., Journal of the American Chemical Society (2003), 125(16), 4702-4703.*
International Search Report for International Application No. PCT/US2009/050635 issued by the European Patent Office, mailed on Nov. 13, 2009.
Levins, C.G., et al., "The synthesis of functionalized nanoscale molecular rods of defined length", *Journal of the American Cancer Society*, 2003, vol. 125, pp. 4702-4703.
Pornsuwan, S., et al., "Flexibility and Lengths of Bis-peptide Nanostructures by Electron Spin Resonance", *Journal of the American Cancer Society*, 2006, vol. 128, pp. 3876-3877.
Gupta, S., et al., "Synthesis of Structurally Diverse Bis-peptide Oligomers", *Journal of Organic Chemistry*, 2006, vol. 71, pp. 8691-8695.

* cited by examiner

*Primary Examiner* — James O. Wilson
*Assistant Examiner* — Cecilia M Jaisle
(74) *Attorney, Agent, or Firm* — RatnerPrestia

(57) ABSTRACT

Functionalized bis-peptides as well as other amide-containing compounds are obtained by acylation of hindered amines. The functionalized bis-peptides are useful as shape-programmable nanostructures that are immune to denaturation and that contain arrays of functional groups having designed catalytic, protein-binding and/or sensor capabilities.

9 Claims, 17 Drawing Sheets

Hindered Amine    Acyl Compound    Acylated Hindered Amine

Hindered Amine    Acyl Compound    Bis-Peptide

ACYLATION OF HINDERED AMINES AND FUNCTIONALIZED BIS-PEPTIDES OBTAINED THEREBY

CROSS-REFERENCE TO RELATED APPLICATIONS

This application is a continuation-in-part of International Application No. PCT/US2009/050635, filed Jul. 15, 2009, and published in English Jan. 21, 2010, as WO 2010/009196, which in turn claims priority from U.S. Provisional Application No. 61/080,861, filed Jul. 15, 2008. Each of these applications is incorporated herein by reference in its entirety for all purposes.

STATEMENT REGARDING FEDERALLY SPONSORED RESEARCH OR DEVELOPMENT

This invention was made with United States Federal Government support under contract number GM067866 (NIH/NIGMS), contract number EUREKA-GM094843-01 (NIH/NIGMS), contract number HDTRA1-09-1-0009 (Defense Threat Reduction Agency; DOD-DTRA), and grant number TG-CHE100059 (National Science Foundation through TeraGrid resources provided by NICS). The U.S. Federal Government has certain rights in this invention.

FIELD OF THE INVENTION

The present invention relates to bis-peptides containing functional groups and also to methods for the acylation of hindered amines.

BACKGROUND OF THE INVENTION

The need for new chemical agents that can modulate protein function in vivo provides a fundamental challenge for chemists. Molecules that are intermediate in size between small molecule drugs (<600 Daltons) and protein therapeutics could provide new chemical entities capable of binding to the large, flat protein surfaces required to modulate a protein function. Bis-peptides potentially could meet this need, but to date synthetic methods for preparing such compounds have not been fully explored or developed, particularly with respect to bis-peptides that contain one or more functional groups that project in defined three dimensional constellations.

Bis-peptides are analogues of peptides, but are derived from bis-amino acids bearing two carboxyl groups and two amino groups. The connection of specific bis-amino acids leads to the formation of bis-peptides with well-defined molecular shapes, which are of great interest for designing nano-structures. Bis-peptides may be spiro-cyclic oligomers or polymers assembled from stereochemically pure, cyclic bis-amino acids. Such bis-amino acids display two alpha-amino acid groups mounted on a cyclic core. In the assembly of bis-peptides, diketopiperazine rings are formed between adjacent monomers to create spiro-ladder oligomers with well-defined three-dimensional structures. The potential advantage of bis-peptides is that the relative position of each monomer's functional group is defined by the monomer's ring structure and stereochemistry in relation to its two immediate neighbors. This is in contrast to proteins, DNA, RNA and unnatural foldamers in which each monomer is joined to its neighbors by one bond and they adopt well-defined three dimensional structures in which monomers interact through many weak non-covalent interactions only after a complex, cooperative folding process that is challenging to accurately model and the outcome of which is difficult to predict.

SUMMARY OF THE INVENTION

We have now discovered a synthetic methodology for the assembly of bis-peptides that makes possible for the first time the controlled placement of functional groups of different types along the length of a bis-peptide molecule. These functional groups can be pendant to the bis-peptide chain, which can be dimeric, oligomeric or polymeric in character. Pre-organized, functionalized bis-peptides can be designed using relatively simple molecular modeling which have three-dimensional structures that are immune to denaturation, thus potentially providing significant advantages over proteins, DNA, RNA and unnatural foldamers. The control of functional group presentation can be determined by the structure of the bis-amino acids used to prepare the bis-peptides. The three-dimensional structure of the bis-peptide backbone and thus the relative orientation of the side-chains (the functional groups) can be varied as desired by controlling the stereochemistry and the sequence of the monomers utilized in constructing the bis-peptide. The constellations of functional groups in the bis-peptide can mimic active sites of proteins and protein binding surfaces. The bis-peptides of the present invention are highly preorganized macromolecules (e.g., having molecular weights of 600 to 2000 Daltons), which can be designed to recapitulate the presentation of the relevant side chains of one partner of a protein-protein interaction, bind the other partner and mediate a biological response.

The invention thus provides a bis-peptide comprising a plurality of diketopiperazine rings, wherein at least one diketopiperazine ring contains a tertiary amide nitrogen atom bearing a pendant functional group.

Also provided by the present invention is a bis-peptide corresponding to the general structure:

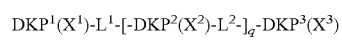

wherein q is 0 or an integer (e.g., 1-50); $DKP^1$, $DKP^2$ and $DKP^3$ are diketopiperazine rings; $X^1$, $X^2$ and $X^3$ are the same or different and are hydrogen or functional groups attached to a tertiary amide nitrogen atom of a diketopiperazine ring, subject to the provisos that i) at least one of $X^1$, $X^2$ or $X^3$ is not hydrogen (in one aspect, at least two of the X groups within the bis-peptide are not hydrogen) and ii) when q is greater than 1, $X^2$ may differ among the $-DKP^2(X^2)-L^2-$ repeating units; and $L^1$ and $L^2$ are the same or different and are linking moieties, each preferably containing two divalent hydrocarbyl or substituted hydrocarbyl groups such as alkylene groups (e.g., $-CH_2-$, $-CH_2CH_2-$) or one tetravalent hydrocarbyl or substituted hydrocarbyl group which are part of a ring structure (in particular, a five- or six-membered ring structure or a ring structure containing fused five- and/or six-membered rings) which also includes an amide nitrogen and a carbon atom of one diketopiperazine ring and a carbon atom of the adjacent diketopiperazine ring, subject to the proviso that when q is greater than 1, $L^2$ may differ among the $-DKP^2(X^2)-L^2-$ repeating units. The configuration of stereocenters within the bis-peptide can be any combination of (S) and (R).

The invention further provides a bis-peptide that includes one or more diketopiperazine rings joining repeating units selected from the following structures

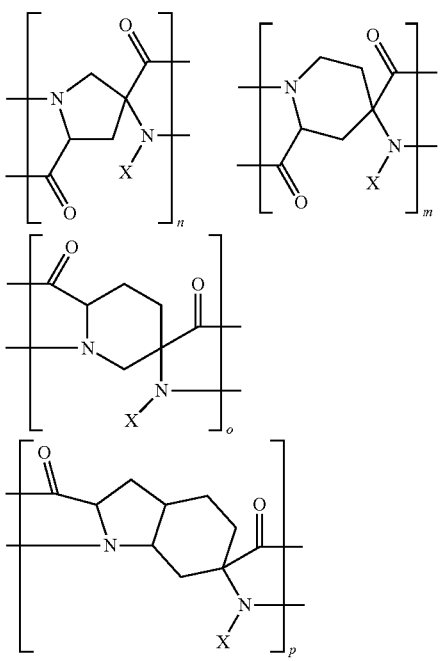

wherein each of n, m, o and p is zero or a positive integer; (n+m+o+p) is greater than or equal to 2; and each X is independently hydrogen or —CH($R^1$)($R^2$) in which $R^1$ and $R^2$ in each unit are independently selected from the group consisting of hydrogen, hydrocarbyl, and substituted hydrocarbyl groups, provided that at least one X in the compound is not hydrogen. The configuration of stereocenters within the bis-peptide can be any combination of (S) and (R).

The present invention also provides a method of acylating a hindered amine, which can be utilized in the synthesis of the above-mentioned bis-peptides. The acylation method comprises reacting a hindered amine having a secondary amine group and a carboxylic acid group alpha to the secondary amine group with an acyl compound containing an activated acyl group. This method can also be adapted for use in synthesizing hindered dipeptides, wherein a first amino acid having a nitrogen atom protected by a protecting group, a carbon atom adjacent to said nitrogen atom substituted with one or two groups other than hydrogen, said groups comprising a total of at least two carbon atoms, and an activated carboxylic acid group is reacted with a second amino acid having a secondary amino group, a free carboxylic acid group, and a carbon atom between said secondary amino group and said carboxylic acid group substituted with one or two groups other than hydrogen, said groups comprising a total of at least two carbon atoms.

DETAILED DESCRIPTION OF THE INVENTION

Figure 1:
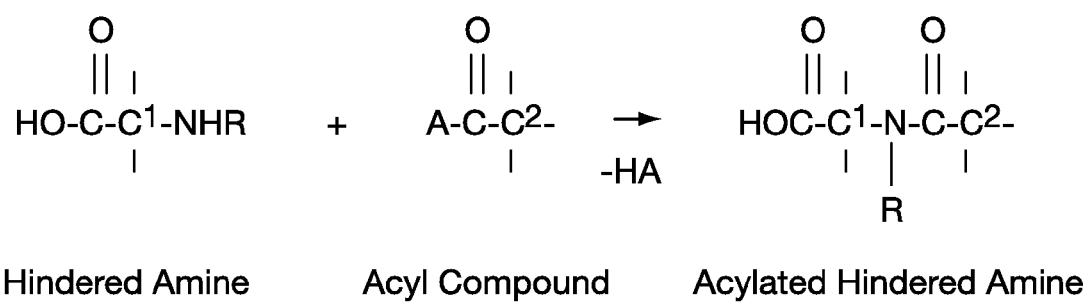
FIG. 1 illustrates the acylation of a hindered amine in accordance with the invention.

We have found that the secondary amide nitrogen between every pair of monomers of a bis-peptide is an ideal location for incorporating additional chemical functionality. Utilizing this position, it is possible to incorporate functionality late in the mono mer synthesis or even on a solid support during assembly of the bis-peptide. For example, a primary amine group can be alkylated with an alkyl halide or the like or reacted with various aldehydes in a reductive amination to introduce the desired functional group and then, in principle, the oligomer or polymer further extended by reaction with another amino acid. However, this synthetic approach does not work well in practice, as the resulting secondary amine is no longer sufficiently nucleophilic to undergo acylation with the next amino acid.

We have now discovered that this problem can be solved by introducing a free carboxylic acid group alpha to the secondary (hindered) amine group. The carboxylic acid group apparently facilitates acylation of the secondary amine group under relative mild conditions, perhaps due to participation by this neighboring group. This result was unexpected, in that a secondary amine group alpha to a carboxylic acid alkyl ester (e.g., —$CO_2CH_3$) reacts sluggishly, if at all, with amino acids, especially hindered amino acids.

The invention provides a unique class of functionalized dimeric, oligomeric and polymeric compounds (functionalized bis-peptides) built from a collection of building blocks (bis-amino acids) which may be assembled in different sequences and in different lengths. Each building block can display a functional group, although non-functionalized building blocks can also be introduced (as spacer repeating units, for example). The functional groups are pendant to the backbone of the bis-peptide, i.e., they extend out or away from the bis-peptide backbone (sometimes also referred to as the bis-peptide scaffold) and thus can be available for interaction with other molecules or chemical species (e.g., complexation, reaction, binding). In one aspect of the invention, the functional group is attached to a nitrogen atom. The invention provides any sequence of bis-amino acid building blocks connected through pairs of amide bonds to create bis-peptides, wherein at least one bis-amino acid building block in the bis-peptide molecule carries a functional group. In one aspect of the invention, a plurality of bis-amino acids in the bis-peptide molecule carry functional groups, wherein functional groups of at least two different types are present in the bis-peptide. In another aspect of the invention, the functional group is attached to a nitrogen atom that is part of a diketopiperazine ring structure in the bis-peptide. Such functionalized nitrogen atoms thus can have a tertiary amide structure. The functional groups may be introduced using different approaches, including a submonomer approach (where an amine group is functionalized during synthesis of the bis-peptide) as well as an approach where building blocks with the functionality already installed are utilized.

In one embodiment, the bis-peptides of the invention are spiroladder macromolecules (oligomers, polymers) having no rotatable bonds in their backbones.

The present invention provides methods for the introduction of a very wide variety of such functional groups in bis-peptides, including, for example, aromatic-containing groups (e.g., phenyl, benzyl, p-cresol, 1-methoxy-benzene, naphthyl, imidazole, 4-methyl-phenol, 1-methoxy-4-methyl-benzene, 2-pyrene, 1-methylimidazole, indole, 2-pyridine, 3-pyridine, triazole, imidazole), carboxylic acid-containing groups (e.g., ethanoic acid, acetic acid, propionoic acid), ester-containing groups (e.g., methyl formate, methyl acetate), amide-containing groups (e.g., ethanoamide, propionamide), hydroxamic acid-containing groups (e.g., carboxhydroxamide, ethanohydroxamide, propionhydroxamide), amine-containing groups (e.g., amine, methanamine, ethanamine, propanamine, N,N-dimethylmethanamine, methyl-guanidine, ethyl-guanidine, propyl-guanidine, dimethylamine, N,N,N-trimethylmethanamine, methylamine, methyl-thiourea, ethyl-thiourea, 1-(3,5-bis(trifluoromethyl)phenyl)-3-ethylthiourea, or 1-(3,5-bis(trifluoromethyl)phenyl)-3-ethylurea), azido-containing groups (e.g., methyl-azide, azide), aliphatic-containing groups (e.g., isopropyl, isobutyl, isopentyl, ethyl, methyl, cyclopentyl, cyclohexyl, 1-methyl-propyl), hydroxyl- or sulfuhydryl-containing groups (e.g., hydroxyl, methyl-hydroxyl, thiol, methyl-thiol), ether- or thioether-containing groups (e.g., methyl-ether, ethyl-ether, methyl-thioether, ethyl-thioether), alkenyl or alkynyl groups (e.g., ethene, allyl, ethyne, propargyl), nucleobase-containing groups (e.g., guanine, adenine, cytosine, thymine). In one aspect of the invention, at least one of the aforementioned functional groups is attached to a carbon atom which in turn is connected to a nitrogen atom, in particular a nitrogen atom that is part of a diketopiperazine moiety contained within the bis-peptide. For example, one of the nitrogen atoms in a diketopiperazine moiety of the bis-peptide may bear a group —CHR$^1$R$^2$, wherein R$^1$ and R$^2$ may be the same or different and may be hydrogen (—H) or one of the aforementioned functional groups. The functional groups may be hydrocarbyl groups (i.e., groups containing only carbon and hydrogen atoms) or substituted hydrocarbyl groups (i.e., groups containing one or more atoms other than carbon and hydrogen atoms, such as oxygen, sulfur, nitrogen and/or halogen atoms). The functional group may be neutral, acidic or basic and may be ionic in character (e.g., a salt).

The preceding list of R1 and R2 groups is exemplary. Additional exemplary R1 and R2 groups may include hydrogen or any of the following:

Ar, (C1-C6)-straight or branched alkyl, (C2-C6)-straight or branched alkenyl or alkynyl, (C5-C7)-cycloalkyl substituted (C1-C6)-straight or branched alkyl, (C5-C7)-cycloalkyl substituted (C3-C6)-straight or branched alkenyl or alkynyl, (C5-C7)-cycloalkenyl substituted (C1-C6)-straight or branched alkyl, (C5-C7)-cycloalkenyl substituted (C3-C6)-straight or branched alkenyl or alkynyl, Ar-substituted (C1-C6)-straight or branched alkyl, Ar-substituted (C3-C6)-straight or branched alkenyl or alkynyl; wherein any one of the CH$_2$ groups of said alkyl chains is optionally replaced by a heteroatom selected from the group consisting of O, S, SO, SO$_2$, and NR; wherein R is selected from the group consisting of hydrogen, (C1-C4)-straight or branched alkyl, (C3-C4)-straight or branched alkenyl or alkynyl, and (C1-C4) bridging alkyl wherein a bridge is formed between the nitrogen and a carbon atom of said heteroatom-containing chain to form a ring, and wherein said ring is optionally fused to an Ar group; wherein Ar is a carbocyclic aromatic group selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroquinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl; wherein Ar is optionally substituted with one or more substituents which are independently selected from the group consisting of hydrogen, halogen, hydroxyl, nitro, —SO$_3$H, trifluoromethyl, trifluoromethoxy, (C1-C6)-straight or branched alkyl, (C2-C6)-straight or branched alkenyl, —O—[(C1-C6)-straight or branched alkyl], O—[(C3-C4)-straight or branched alkenyl], —O-benzyl, —O-phenyl, 1,2-methylenedioxy, —NR$^5$R$^6$, carboxyl, —N—(C1-C5-straight or branched alkyl or C3-C5-straight or branched alkenyl) carboxamides, -N,N-di-(C1-C5-straight or branched alkyl or C3-C5-straight or branched alkenyl) carboxamides, morpholinyl, piperidinyl, —O-M, —CH$_2$—(CH$_2$)$_q$-M, —O—(CH$_2$)$_q$-M, —(CH$_2$)$_q$—O-M, and —CH═CH-M; wherein R$^5$ and R$^6$ are independently selected from the group consisting of hydrogen, (C1-C6)-straight or branched alkyl, (C3-C6)-straight or branched alkenyl or alkynyl and benzyl; wherein M is selected from the group consisting of 4-methoxyphenyl, 2-pyridyl, 3-pyridyl, 4-pyridyl, pyrazyl, quinolyl, 3,5-dimethylisoxazoyl, 2-methylthiazoyl, thiazoyl, 2-thienyl, 3-thienyl and pyrimidyl; and q is 0-2. R$^1$ and R$^2$ may also be linked to each other to form a ring, such as a hydrocarbyl or substituted hydrocarbyl ring (e.g., cyclohexyl, cyclopentyl).

One or both of the end groups of the bis-peptide may contain a diketopiperazine ring in which a carbon atom in the diketopiperazine ring of the end group bears at least one pendant functional group other than hydrogen. This pendant functional group may be any of the types of functional groups previously mentioned. The stereochemistry of the ring carbon atom to which the functional group or functional groups is or are attached may be selected and controlled as may be desired, e.g., (S) or (R). The functional group at this position may be utilized to introduce a label, such as a fluorescent label (a functional group capable of fluorescing, i.e., a fluorescent tracer such as fluorescein) into the bis-peptide molecule.

The functionalized bis-peptides of the present invention include a large collection of compounds created by a novel synthetic process described herein. Like proteins, these compounds position one or more functional groups in precise arrangements in three-dimensional space relative to the backbone. For example, the functionalized bis-peptide may position an imidazole and a base and allow the stereoselective acylation of inexpensive racemic alcohols to create a separable mixture of one stereochemically pure alcohol and one stereochemically pure ester. Another functionalized bis-peptide may present three hydrophobic groups in an arrangement that mimics one face of an alpha helix, disrupts the p53/HDM2 interaction and cause cancer cells to commit apoptosis (cell suicide).

The invention allows the placement of a variety of chemical functionality on a rigidified macromolecular scaffold. The novel features of the invention include the conformational rigidity of the scaffold, achieved by connecting the molecular building blocks through pairs of amide bonds as well as by incorporating functional groups onto the monomers that, prior to this invention, rendered the building blocks completely inert and terminated the synthesis.

With functionalized bis-peptides, because of their fused-ring structure, one can know precisely where functional groups will appear in three-dimensional space. Because the sequence of building blocks within the bis-peptide can be specified, it is possible to control the position of functional groups in space.

Conformational rigidity of the macromolecule allows pre-organization of the functional groups, thus enhancing their ability to carry out their unique function.

The invention also provides methods for making such compounds. The methods allow the user to incorporate the functional groups onto the building blocks and assemble them into the functionalized bis-peptides. The inventors are unaware of any other practical way of achieving this objective.

Without wishing to be bound by theory, the acylation of the functionalized secondary amine may occur by the activation of a free carboxylic acid to an anhydride alpha to the hindered amine, followed by a novel rearrangement that transfers the acyl group to the amine.

The methods of this invention allow the creation of highly hindered tertiary amides in peptides and highly substituted diketopiperazines that are very difficult to synthesize by other means. Hindered amide bonds and highly substituted diketopiperazines are valuable as motifs in drug synthesis.

Thus, in accordance with the invention, a hindered amide is obtained by acylating a hindered amine, wherein the hindered amine has a secondary amine group and a carboxylic acid group alpha to the secondary amine group and is reacted with an acyl compound containing an activated acyl group. FIG. 1 illustrates this type of reaction, where R is a substituent other than hydrogen such as a hydrocarbyl group, substituted hydrocarbyl group, or protecting group and Z is an activating group such as F, OAt or the like. Substituent R may form part of a ring structure including the nitrogen atom of the secondary amine group and the carbon atom to which the free carboxylic acid group is attached ($C^1$ in FIG. 1). In one embodiment, the hindered amine bears at least one substituent other than hydrogen and the carboxylic acid group on the carbon atom to which both the secondary amine group and the carboxylic acid group are attached ($C^1$ in FIG. 1). Such substituent(s) can be any of the functional groups previously described. In one embodiment, the acyl compound is also hindered. For example, the carbon atom adjacent to the C=O group in the acyl compound ($C^2$ in FIG. 1) can be substituted with two or more functional groups other than hydrogen, with any of the functional groups previously described being suitable for such purpose (e.g., hydrocarbyl groups and/or substituted hydrocarbyl groups). In one aspect of the invention, the acyl compound bears an amine group and at least one substituent other than hydrogen (e.g., one of the functional groups previously described) on the carbon atom adjacent to the acyl group. This amine group can be a secondary amine group, wherein the nitrogen atom bears, in addition to a hydrogen atom, a functional group (which can be any of the functional groups previously described) or to a protecting group (i.e., a group capable of being removed and replaced by a hydrogen atom following a reaction of the acyl compound in which the protected amine group does not participate, e.g., an Fmoc group, a t-Boc group, a Cbz group or the like). The secondary amine group may, for example, bear a functional group having structure —CH($R^1$)($R^2$) in which $R^1$ and $R^2$ are independently selected from the group consisting of hydrogen, hydrocarbyl, and substituted hydrocarbyl groups. The activated acyl group can be any derivative of a carboxyl group that is more susceptible to nucleophilic attack (specifically, to attack by a secondary amine) than a free carboxylic acid group or a methyl ester group. Illustrative examples of suitable activated acyl groups include acid fluorides, At esters, Bt esters, N-hydroxysuccinimide esters, pentafluorophenyl esters, O-acyl-ureas and the like. Any of the coupling agents known in the art of peptide coupling can be used to introduce an activated acyl group into the acyl compound (e.g., by conversion of a free carboxylic acid group) including, for example, HATU (2-(1H-7-azabenzotriazol-1-yl)-1,1,3,3-tetramethyl uronium hexafluorophosphate), BOP (benzotriazol-1-yl-oxy-tris(dimethylamino)phosphonium hexafluorophosphate), PyBOP (1H-1,2,3-benzotriazol-1-yloxy)-tris(pyrrolidino)-phosphonium hexafluorophosphate), HBTU (O-benzotriazole-N,N,N',N'-tetramethyl uronium hexafluorophosphate), N-hydroxybenzotriazole (HOBT), O-(1H-benzotriazole-1-yl)-N,N,N',N'-tetramethyluronium tetrafluoroborate (TBTU), DCC (dicyclohexylcarbodiimide), DIC (diisopropylcarbodiimide), chloro-N,N,N',N'-tetramethylformamidinium hexafluorophosphate or the like. Uronium and phosphonium salts of non-nucleophilic anions such as tetrafluoroborate or hexafluorophosphate are particularly useful. In one embodiment, an onium coupling agent is employed.

Figure 2:
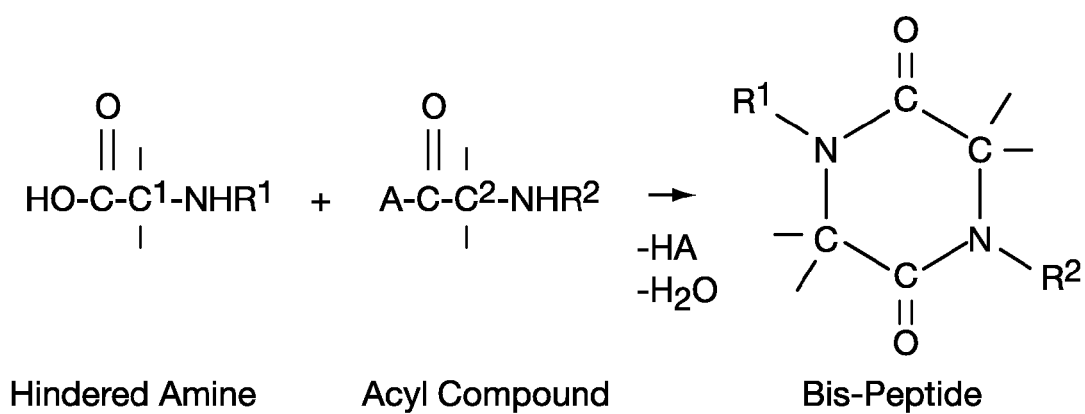
FIG. 2 illustrates the formation of a bis-peptide having a diketopiperazine ring from a hindered amine and an acyl compound in accordance with the invention.

In one aspect of the invention, which is useful in the construction of bis-peptides, the acyl compound bears an amine group (which can be a secondary or protected amine group) alpha to the activated acyl group and the initial acylation yields an amide intermediate which undergoes dehydration and ring closure involving the amine group of the acyl compound and the carboxylic acid group of the hindered amine to form a diketopiperazine ring. The dehydration may be facilitated by the use of a dehydrating agent such as a diimide (e.g., diisopropylcarbodiimide, also known as DIC). This type of reaction is illustrated in FIG. 2, where $R^1$ and $R^2$ are the same or different and are independently selected from hydrocarbyl groups, substituted hydrocarbyl groups and protecting groups and A has the same meaning as in FIG. 1. One or both of $R^1$ and $R^2$ may form part of a ring structure which also includes the nitrogen atom of a secondary amine group and the carbon atom adjacent to that secondary amine group marked in FIG. 2 as $C^1$ or $C^2$.

In one embodiment of the invention, a functionalized bis-peptide is sequentially assembled in accordance with the following general procedure. A first building block (which can be attached to a resin or other solid support, if so desired) is selected which contains both a secondary amine group (where the amine nitrogen may be part of a ring structure, for example) and a free carboxylic acid group alpha to that secondary amine group (for example, the free carboxylic acid group may be attached to a carbon atom adjacent to the amine nitrogen atom, where the carbon atom is part of the same ring structure as the amine nitrogen atom). This first building block is reacted with a second building block which contains a secondary amine group bearing a pendant functional group and an activated acyl group (e.g., an At ester) alpha to the secondary amine group as well as a protected amine group (e.g., NCbz) and a protected carboxylic acid group (e.g., —CO₂-tBu) alpha to the protected amine group. This reaction yields a bis-peptide containing a diketopiperazine ring formed by the interaction of the secondary amine group and free carboxylic acid group of the first building block with the secondary amine group and activated acyl group of the second building block, with the protected amine group and protected carboxylic acid group of the second building block remaining intact in the bis-peptide. These protecting groups are then removed to provide a secondary amine group and a free carboxylic acid group alpha to the secondary amine group, which are subsequently reacted similarly with a third building block which contains a secondary amine group bearing a pendant functional group (which can be different from the functional group in the second building block) and an activated acyl group alpha to the secondary amine group as well as a protected amine group and a protected carboxylic acid group alpha to the protected amine group. Similar cycles of reaction, deprotection and reaction with further building blocks as may be repeated as desired to increase the length of the bis-peptide macromolecule and introduce different functional groups along the backbone. The stereochemistry and structure of the individual building blocks may be selected so as to vary and control the three-dimensional shape of the bis-peptide. The bis-peptide may be end-capped with various compounds to introduce further functionality at the terminus. For example, the secondary amine group and free carboxylic acid group alpha to the secondary amine group at the bis-peptide terminus can be reacted with a functionalized mono-amino acid to form a diketopiperazine ring at the terminus bearing a functional group attached to a carbon atom of the diketopiperazine ring.

In another embodiment of the invention, a functionalized bis-peptide is sequentially assembled in accordance with the following general procedure. A first building block (which can be attached to a resin or other solid support, if so desired) is selected which contains both a protected primary amine group (having the structure —NHPr, for example, where Pr is a protecting group such as Fmoc) and a protected carboxylic acid group alpha to that protected primary amine group (for example, the protected carboxylic acid group may be a —C(=O)ODmab group). The protected primary amine group is deprotected to provide a primary amine group, which is then functionalized using reductive amination (reaction with an aldehyde or ketone) or alkylation (reaction with an alkyl halide, for example) to convert the primary amine group to a secondary amine group bearing a functional group. The protected carboxylic acid group is then converted to an activated acyl group (for example, by deprotection of the carboxylic acid group and reaction of the resulting free carboxylic acid with a peptide coupling agent). This product is reacted with a second building block which contains a secondary amine group (which can be part of a ring structure, for example) and a free carboxylic acid group alpha to the secondary amine group as well as a protected primary amine group (e.g., NHFmoc) and a protected carboxylic acid group (e.g., —CO₂-Dmab) alpha to the protected primary amine group. This reaction yields a bis-peptide containing a diketopiperazine ring formed by the interaction of the functionalized secondary amine group and activated acyl group of the first building block with the secondary amine group and free carboxylic acid group of the second building block, with the protected primary amine group and protected carboxylic acid group of the second building block remaining intact in the bis-peptide. The protecting group on the protected primary amine group is then removed to provide a primary amine group, which is thereafter functionalized to introduce a functional group onto the nitrogen atom which is the same as or different from the first functional group incorporated into the bis-peptide. The protected carboxylic acid group is then deprotected to provide a free carboxylic acid group alpha to the functionalized secondary amine group. The bis-peptide is subsequently reacted with a third building block which contains a secondary amine group and a free carboxylic acid group alpha to the secondary amine group as well as a protected primary amine group and a protected carboxylic acid group alpha to the protected primary amine group. Similar cycles of deprotection, functionalization, activation of an acyl group and reaction with further building blocks as may be repeated as desired to increase the length of the bis-peptide macromolecule and introduce different functional groups along the backbone. The stereochemistry and structure of the individual building blocks may be selected so as to vary and control the three-dimensional shape of the bis-peptide. The bis-peptide may be end-capped with various compounds to introduce further functionality at the terminus.

In still another embodiment of the invention, a bis-peptide is synthesized starting with a first building block (which may or may not be immobilized) that contains a functionalized secondary amine group (e.g., —NHR, where the nitrogen atom is not part of a ring structure and R is a functional group) and an activated acyl group alpha to the functionalized secondary amine group. This first building block is reacted with a second building block containing a secondary amine group (which can be part of a ring structure) and a free carboxylic acid group alpha to the secondary amine group as well as a functionalized secondary amine group (where the functional group may be the same as or different from the functional group in the first building block) and a protected carboxylic acid group (e.g., —CO₂Dmab) alpha to the functionalized secondary amine group. This reaction yields a bis-peptide containing a diketopiperazine ring formed by the interaction of the functionalized secondary amine group and activated acyl group of the first building block with the secondary amine group and free carboxylic acid group of the second building block, with the protected carboxylic acid group of the second building block remaining intact in the bis-peptide. The protected carboxylic acid group present in the bis-peptide may be converted to an activated acyl group and the bis-peptide further extended in a similar manner with a third building block containing a secondary amine group and a free carboxylic acid group alpha to the secondary amine group as well as a functionalized secondary amine group (where the functional group may be the same as or different from the functional group in the first and second building blocks) and a protected carboxylic acid group alpha to the functionalized secondary amine group. Additional cycles of reaction, deprotection, activation and reaction may be carried out with still more such building blocks to introduce different functional groups along the backbone and influence the three-dimensional shape of the bis-peptide. The bis-peptide may be end-capped with various compounds to introduce further functionality at the terminus.

The acylation methods described herein can also be readily adapted for use in preparing hindered dipeptides, wherein a first amino acid having a nitrogen atom protected by a protecting group, an activated acyl group, and a carbon atom adjacent to said nitrogen atom and between the nitrogen atom and the activated acyl group, wherein the carbon atom is substituted with one or two groups other than hydrogen, these groups comprising a total of at least two carbon atoms, is reacted with a second amino acid having a secondary amino group, a free carboxylic acid group, and a carbon atom between said secondary amino group and said carboxylic acid group substituted with one or two groups other than hydrogen, said groups comprising a total of at least two carbon atoms. The hindered dipeptide thereby obtained may have the general structure:

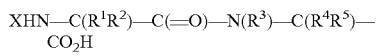

wherein X is a protecting group, $R^1$, $R^2$, $R^4$ and $R^5$ are the same or different and are independently selected from the group consisting of hydrogen, hydrocarbyl groups and substituted hydrocarbyl groups, subject to the provisos that $R^1$ and $R^2$ are not both hydrogen and $R^4$ and $R^5$ are not both hydrogen, and $R^3$ is a hydrocarbyl group or substituted hydrocarbyl group. $R^1$, $R^2$, $R^3$, $R^4$ and $R^5$ may, for example, be any of the functional groups previously described. The activated acyl group may be an acid fluoride or an At ester, for example. The first amino acid may have the general structure:

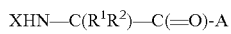

wherein X is a protecting group, $R^1$ and $R^2$ are the same or different and are independently selected from the group consisting of hydrogen, hydrocarbyl groups and substituted hydrocarbyl groups, subject to the proviso that $R^1$ and $R^2$ are not both hydrogen, and A is an activating group (e.g., F, OAt). The second amino acid may have the general structure:

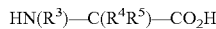

wherein $R^3$ is a hydrocarbyl group or substituted hydrocarbyl group, and $R^4$ and $R^5$ are the same or different and are independently selected from the group consisting of hydrogen, hydrocarbyl groups and substituted hydrocarbyl groups, subject to the proviso that $R^4$ and $R^5$ are not both hydrogen. The protecting group may be an Fmoc group, a Cbz group or a t-Boc group or any other group capable of being removed and replaced by a hydrogen atom following a reaction in which the protected amine group does not participate.

Bis-amino acid monomers may be used to prepare the bis-peptides of the present invention. Such monomers may comprise two alpha-amino acids mounted on a cyclic core. Such monomers may thus constitute chiral, cyclic building blocks. The cyclic core may be a five- or six-membered ring or a ring structure comprised of a five-membered ring fused with a six-membered ring, for example. Typically, the ring or ring structure includes a nitrogen atom as part of the ring or ring structure. Such rings/ring structures provide linkages between the diketopiperazine rings in a bis-peptide macromolecule. The amino acids may be suitably protected for the synthesis of bis-peptide oligomers and polymers. For example, the amine group and/or the carboxylic acid group of each amino acid may be protected so as to render that group unreactive during reaction of the monomer with another species, with the protecting group subsequently being removed so as to render the amine group or carboxylic acid group available for reaction. Each monomer may have a distinct stereochemistry that defines its shape and the shape that it imparts to bis-peptides into which it is incorporated. The bis-amino acid monomer may be functionalized (i.e., an amine group in the building block may bear a functional group). Alternatively, unfunctionalized bis-amino acid monomers may be used to prepare a bis-peptide, wherein an amine group is functionalized after the monomer is incorporated into the bis-peptide.

Bis-amino acid monomers are known in the art and are described, for example, in Levins et al., J. Am. Chem. Soc., Vol. 124, 2003, pp. 4702-4703; Schafmeister et al., Accts. Chem. Res., Vol. 41, No. 10, October 2008, pp. 1387-1398; Gupta et al., Org. Lett., No. 7, 2005, pp. 2861-2864; Habay et al., Org. Lett., No. 6, 2004, pp. 3369-3371; US 2004-0082783; and US 2004-0077879, each of which is incorporated herein by reference in its entirety for all purposes.

The bis-peptides of the present invention may be synthesized in solution using one or more suitable solvents. Solid-phase synthesis techniques may also be utilized, wherein a solid, insoluble resin or other support having functional groups (linkers) on which the bis-peptide can be built is employed. Suitable functional groups include, for example amine groups (e.g., —$NH_2$) and hydroxyl groups (—OH). Aminomethyl polystyrene resins may be utilized. The bis-peptide remains covalently attached to the resin, which may, for example, be in the form of beads, until cleaved from the resin by a reagent such as trifluoroacetic acid. The bis-peptide is thus immobilized on the solid-phase resin during synthesis and can be retained on the resin during a filtration process, wherein liquid-phase reagents and soluble by-products of synthesis are flushed away. The general principle of solid-phase synthesis is one of repeated cycles of coupling-deprotection. That is, a first building block is attached to a resin such that the resin-attached building block contains a free primary or secondary amine group (in one embodiment, a primary amine group in the first building block, after being attached to the solid support is converted to a secondary amine group in which the nitrogen bears a functional group, e.g., a functional group —$CH(R^1)(R^2)$, using reductive amination involving an aldehyde or ketone, halide displacement involving an alkyl halide or other suitable method). This amine group of the first building block is then coupled to a second building block containing an N-protected amine group as well as a carboxylic acid group (in one embodiment, an activated acyl group) to form an amide bond. The amine group of the second building block is then deprotected, revealing a new free amine group to which a further building block may be attached. The structures of the successive building blocks may be selected such that following formation of the initial amide bond, a second amide bond is formed between adjacent building blocks and a diketopiperazine ring is formed. Additionally, the building blocks employed may contain different functional groups attached to the secondary amine nitrogen of each building block, resulting in the production of an oligomeric bis-peptide having different pendant functional groups along its backbone, with the placement of the different functional groups being controlled as desired by the order in which the building blocks are reacted with the growing chain.

In solution phase synthesis, the development of optimized purification protocols for each intermediate requires a great deal of time. Solid state synthesis does not involve purification of intermediates, greatly accelerating the rate at which bis-peptides can be synthesized. Solution phase synthesis requires slightly lower quantities of building block because couplings are performed with stoichiometric amounts of monomers. However, the purified yields of bis-peptide intermediates are generally 60-70%, so the savings do not present a compelling advantage for solution phase synthesis.

Figure 3:
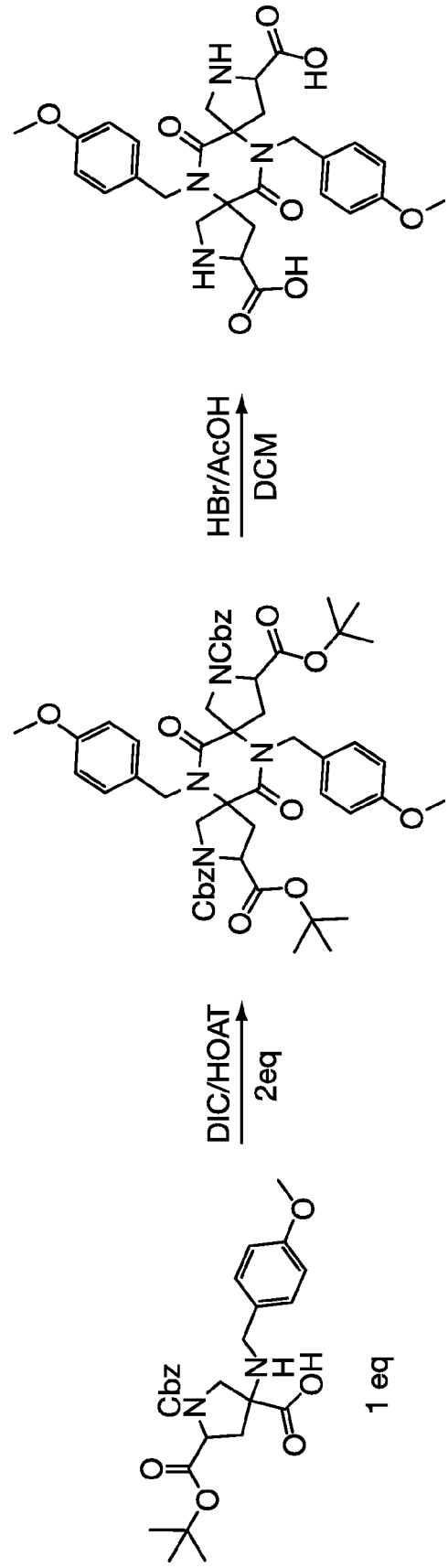
FIG. 3 illustrates the preparation of a hexasubstituted diketopiperazine in accordance with the invention.

Hexasubstituted diketopiperazines may also be prepared in accordance with the present invention, either in solution or by means of solid state synthesis. FIG. 3 illustrates an example of a solution phase synthesis of a symmetric hexasubstituted diketopiperazine, where R may be any of the functional groups previously disclosed. Such hexasubstituted diketopiperazines may be suitably protected to also be incorporated into a bis-peptide oligomer or polymer or used as an independent scaffold.

GLOSSARY OF ABBREVIATIONS

ACN: acetonitrile
AcOH: acetic acid

At: 7-azabenzotriazole
Bn: benzyl
Boc (also referred to as tBoc): t-butyloxycarbonyl
Bt: benzotriazole
Cbz: carbobenzyloxy
DCC: dicyclohexylcarbodiimide
DCM: dichloromethane
DEA: diethylamine
DIC: diisopropylcarbodiimide
DIPEA: diisopropylethylamine
Dmab: 4-{N-[1-(4,4-dimethyl-2,6-dioxocyclohexylidene)-3-methylbutyl]amino}benzyl ester (see FIG. 12)
DMAP: dimethylaminopyridine
DMF: dimethylformamide
Fmoc: 9-Fluorenylmethyloxycarbonyl
HMBA: 4-hydroxymethylbenzoic acid
MeIM: N-methylimidazole
MSNT: 1-(mesitylenesulfonyl)-3-nitro-triazole
OAt: 1-oxy-7-azabenzotriazole
Pip: piperidine
TFA: trifluoroacetic acid
TIS: triisopropylsilane Although the invention is illustrated and described herein with reference to specific embodiments, the invention is not intended to be limited to the details shown. Rather, various modifications may be made in the details within the scope and range of equivalents of the claims without departing from the invention.

EXAMPLES

Example 1

The following examples illustrate the synthesis of different functionalized bis-peptides in accordance with the present invention using a sequential solution phase approach.

Figure 4:
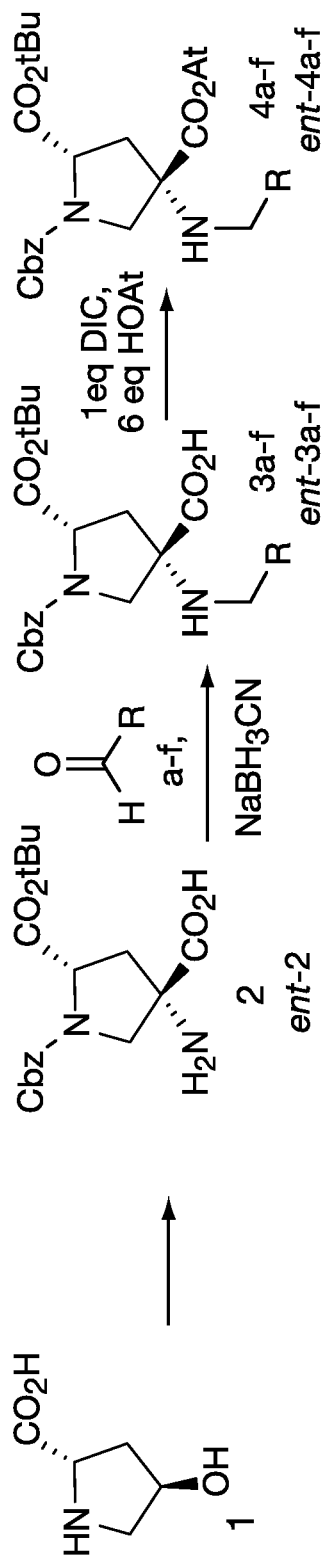
FIG. 4 illustrates the synthesis of functionalized building blocks useful in the practice of the invention.

Amino acids 2 and ent-2 (see FIG. 4) were synthesized in 5 and 7 steps respectively from trans-L-4-hydroxyproline 1 in 49% and 18% overall yield using the procedures described in Schafmeister et al., Acc. Chem. Res. 2008, 41, 1387-1398. The synthesis of each amino acid involved only one chromatographic step. The amino acids 2 and ent-2 were functionalized on the amine nitrogen using reductive amination with the aldehydes a-f shown in Table 1 to form compounds 3a-f and ent-3a-f (FIG. 4) with near quantitative yield. Aldehydes a-f were selected for the purpose of demonstrating that a variety of proteogenic and non-proteogenic functional groups can be used in the present invention. A consequence of the hindered nature of the N-alkyl-alpha,alpha-disubstituted amino acids 3a-f and ent-3-a-f is that the carboxylic acid group of each compound can be activated as the 7-azabenzotriazole (—At) ester to form compounds 4a-f and ent-4-a-f (FIG. 4). Surprisingly, we found that these active esters do not spontaneously self-react and remain monomeric and active in DMF/$CH_2Cl_2$ solutions for several hours at room temperature.

TABLE 1

| Compound | Aldehyde | R = |
|---|---|---|
| 3a/ent-3a | benzaldehyde | phenyl |
| 3b/ent-3b | p-methoxybenzaldehyde | p-methoxyphenyl |
| 3c/ent-3c | 1-naphthaldehyde | 1-naphthyl |
| 3d/ent-3d | $(H_3C)_2CHC(=O)H$ | isopropyl |
| 3e/ent-3e | $HC(=O)CH_2CH_2NHCbz$ | $—CH_2CH_2NHCbz$ |
| 3f/ent-3f | $HC(=O)C(=O)OBn$ | $—C(=O)OBn$ |

Figure 5:
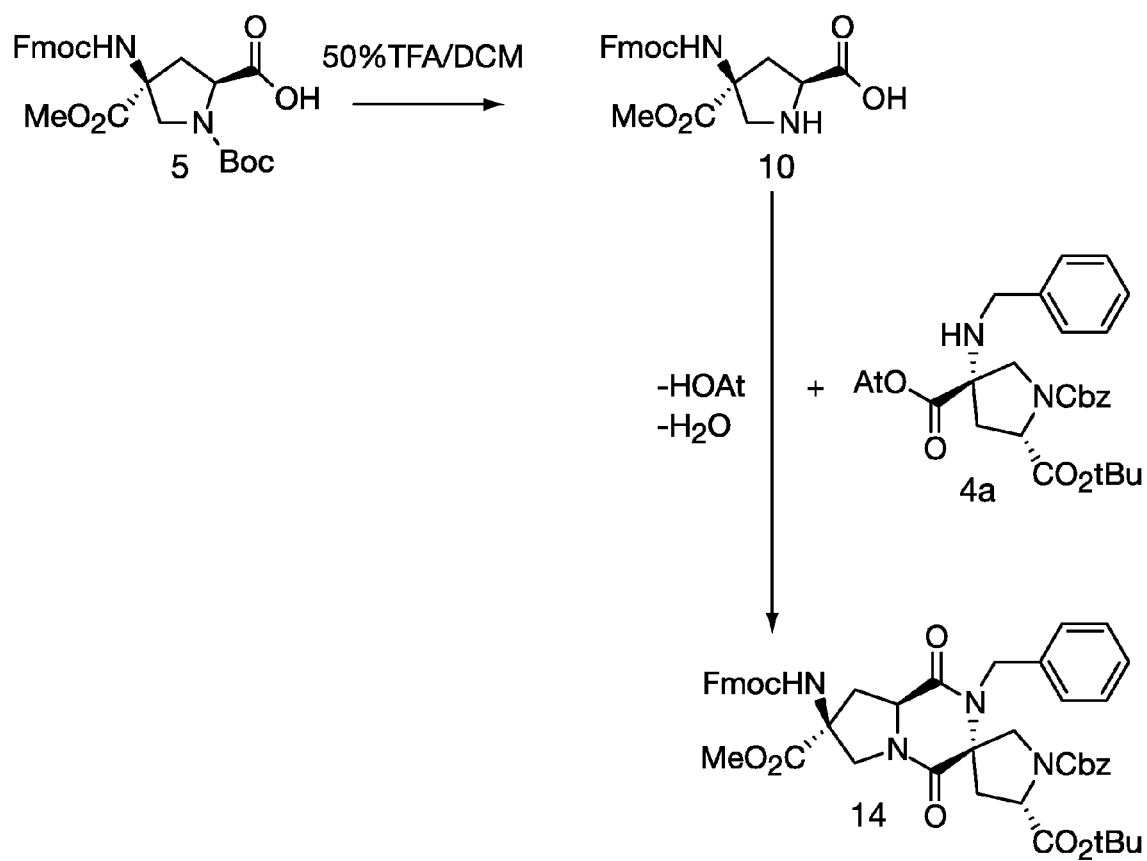
FIGS. 5 and 6 illustrate the assembly of a functionalized bis-peptide in accordance with the invention.
Figure 6:
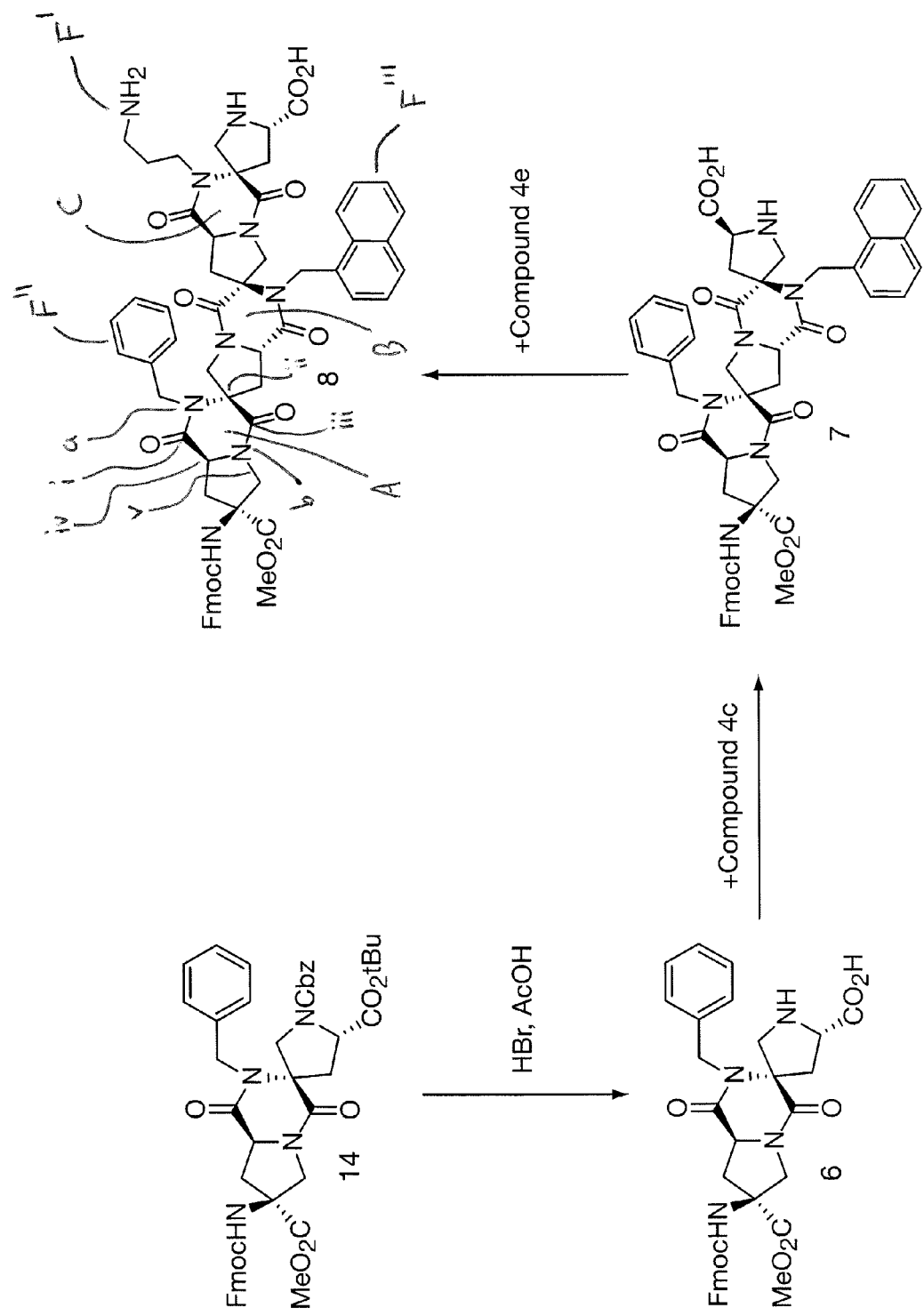

To synthesize functionalized bis-peptide 8 (see FIG. 6), protected bis-amino acid 5 (FIG. 5) was used as a starting material. This compound was prepared in accordance with the procedures described in Schafmeister et al., Acc. Chem. Res. 2008, 41, 1387-1398. The Boc group was removed with 50% trifluoroacetic acid (TFA/$CH_2Cl_2$) to produce compound 10, which was then combined with active ester 4a and stirred at room temperature overnight (2 eq DIPEA, 1:2 DMF/DCM) to provide a mixture of a single amide coupling product and the desired diketopiperazine 14. One equivalent of diisopropylcarbodiimide (DIC) was added to dehydrate the single amide coupling product and increase the yield of diketopiperazine 14. Diketopiperazine 14 was treated with HBr in acetic acid (1:1 33% HBr in AcOH/DCM) to remove the t-butyl and Cbz protecting groups to form amino acid 6 (FIG. 6), which was isolated by $C_{18}$ reverse phase HPLC in 68% recovered yield relative to compound 5. This process was repeated with a new monomer, combining 6 and the activated, 2-methylenenaphthalene functionalized bis-amino acid 4c to form 7 (77% yield from 6, following $C_{18}$ RP-HPLC) following treatment with DIC and HBr in acetic acid. The process was then repeated for a third time, wherein compound 7 was combined with the activated, carboxy-benzoyl amino-propyl functionalized bis-amino acid 4e to provide functionalized bis-peptide 8 (59% yield from 7, following $C_{18}$ RP-HPLC) after treatment with DIC and HBr in acetic acid.

Example 2

Figure 7:
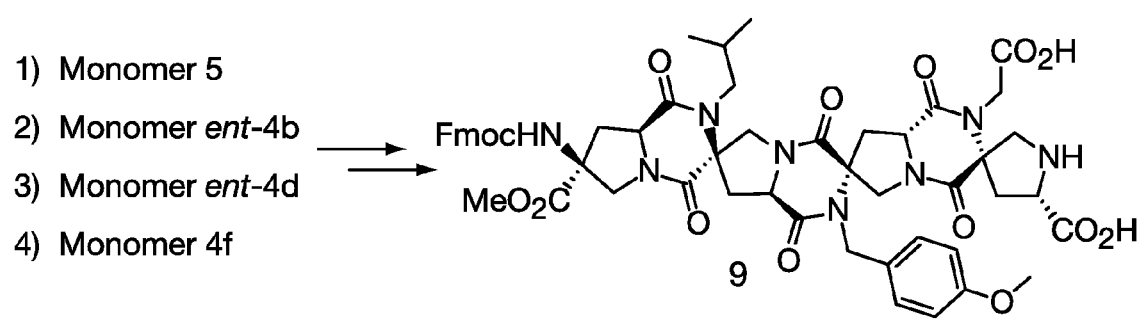
FIG. 7 illustrates the assembly of another functionalized bis-peptide in accordance with the invention.

Functionalized bis-peptide 9 (FIG. 7) was similarly synthesized using a different sequence of functionalized monomers (Compound 5, Compound ent-4b, Compound ent-4d, Compound 4f) with similar recovered yields. The compositions of functionalized bis-peptides 8 and 9 were verified by high-resolution mass spectrometry and the structures were validated using two-dimensional nuclear magnetic resonance experiments.

Examples 3-13

These examples demonstrate the preparation of highly hindered dipeptides in accordance with the present invention.

The dipeptides listed in Table 2 were synthesized by combining an Fmoc-amino acid fluoride with an excess (4 eq.) of an unprotected amino acid dissolved in hexafluoroisopropanol (0.2M). The acid fluorides were obtained using a slight modification of the procedure described in Kaduk et al., Lett. Pept. Sci. 1996, 2, 285-288. Before adding the acid fluoride, the amino acid solution was prewarmed to 55° C. The mixture was allowed to react at 55° C. for varying amounts of time (depending upon the amino acid) and then subjected to reverse-phase high performance liquid chromatography with mass spectrometry (HPLC-MS). Fmoc-amino acids activated as 1-oxy-7-azabenzotriazole (OAt) esters using diisopropylcarbodiimide (DIC) and 1-hydroxy-7-azabenzotriazole (HOAt) also produced dipeptides, but these reactions were found to be about 50% slower than those using acid fluorides.

TABLE 2

| Example | Dipeptide | % Yield | Rxn. Time, min. |
|---|---|---|---|
| 3 | Fmoc-Aib-NMeVal-OH | 80 | 60 |
| 4 | Fmoc-Aib-(S)-Tic-OH | 86 | 60 |
| 5 | Fmoc-Aib-NMeAib-OH | 60 | 60 |
| 6 | Fmoc-(S)-NMeVal-(S)-NMeVal-OH | 78 | 5 |
| 7 | Fmoc-(S)-NMeVal-(S)-Tic-OH | 80 | 5 |

TABLE 2-continued

| Example | Dipeptide | % Yield | Rxn. Time, min. |
|---|---|---|---|
| 8 | Fmoc-(S)-NMeVal-NMeAib-OH | 68 | 5 |
| 9 | Fmoc-(S)-NMeVal-Sar-OH | 78 | 5 |
| 10 | Fmoc-Ac$_5$c-NMeVal-OH | 74 | 45 |
| 11 | Fmoc-Ac$_5$c-(S)-Tic-OH | 79 | 45 |
| 12 | Fmoc-Ac$_5$c-NMeAib-OH | 60 | 45 |
| 13 | Fmoc-Ac$_5$c-Sar-OH | 78 | 45 |

Aib = aminoisobutyric acid
Ac$_5$c = aminocyclopentanecarboxylic acid
Val = valine
Tic = 1,2,3,4-tetrahydroisoquinoline-3-carboxylic acid
Sar = sarcosine Example 14

Figure 8:
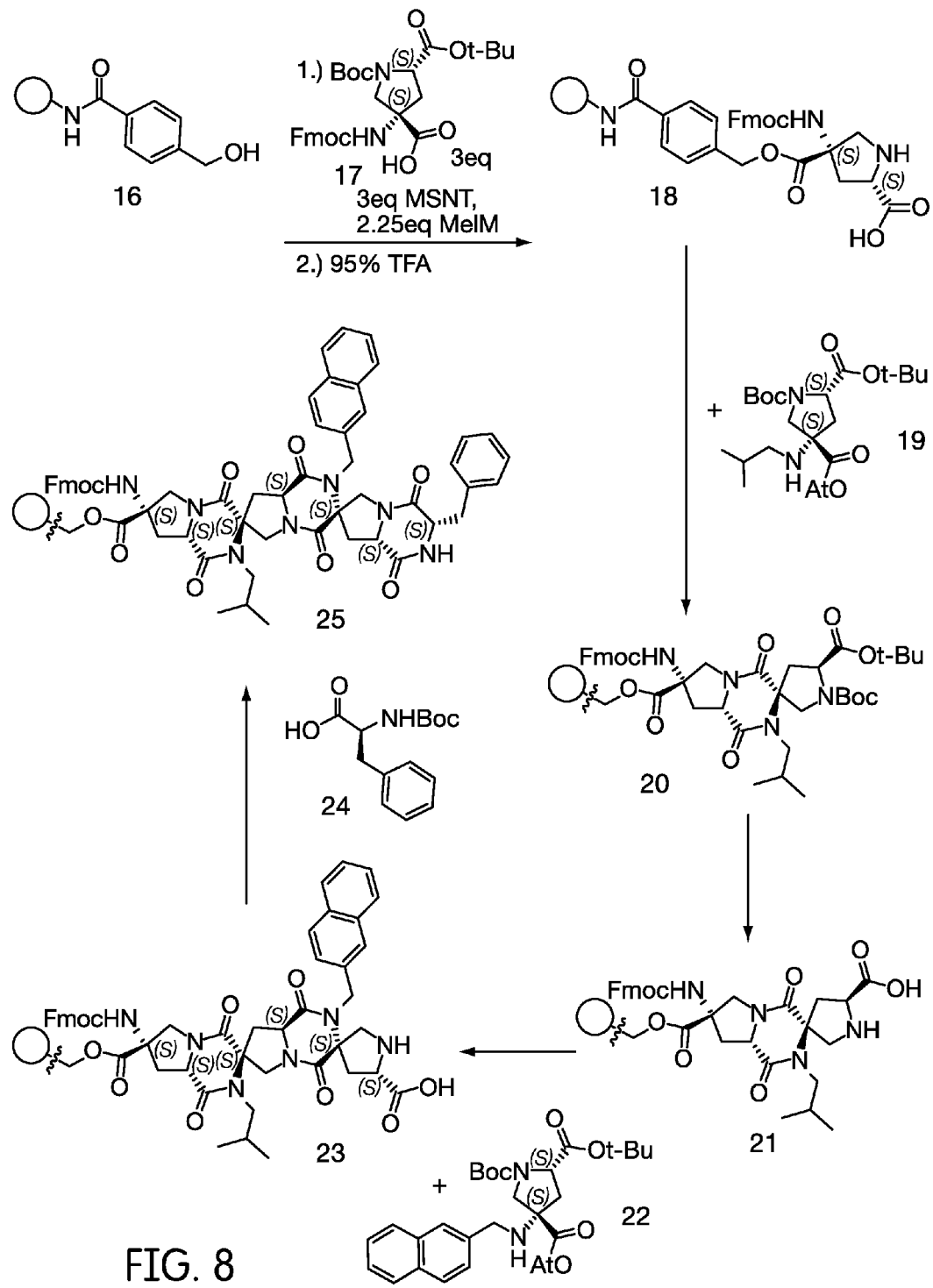
FIG. 8 illustrates the assembly of a bis-peptide bearing isobutyl, naphthyl and benzyl functional groups in accordance with the invention.

This example demonstrates the preparation of p53 alpha-helix mimics in accordance with the invention using solid state synthesis techniques. Building block 17 is prepared by treating compound 35 (see FIG. 15) with 1) H$_2$, Pd/C and 2) Boc$_2$O, DIPEA, which results in the replacement of the Cbz group attached to the ring nitrogen with a Boc group. An HMBA resin 16 is reacted with building block 17 in the presence of 3 eq MSNT and 2.25 eq MeIM to yield resin-immobilized building block 18 as illustrated in FIG. 8, following removal of the t-butyl and Boc protecting groups with 95% TFA. Building block 19 is reacted with resin-immobilized building block 18 and the resulting product treated with DIC/HOAT (1 eq DIC, 6 eq HOAT, 1:2 DMF/DCM, 1.5 hours, RT) to facilitate dehydration of what is believed to be an amide intermediate, thereby yielding bis-peptide 20. Treatment of bis-peptide 20 with 95% TFA/5% TIS (2×1 hour) removes the t-butyl and Boc protecting groups to produce resin-immobilized bispeptide 21, which contains an isobutyl functional group attached to an amide nitrogen atom of the diketopiperazine ring in the bis-peptide and an amino acid functional group at its terminus.

Bis-peptide 21 is further extended and functionalized by reaction with building block 22, DIC/HOAT and 95% TFA to yield resin-immobilized bis-peptide 23, which contains a naphthyl-functionalized amide nitrogen in the second diketopiperazine ring as well as an amino acid functional group at its terminus.

Further extension and functionalization of bis-peptide 23 is accomplished by reaction with building block 24+HATU, 95% TFA, and DIC/HOAT to yield resin-immobilized bis-peptide 25, which contains a benzyl functional group attached to a carbon atom of the third diketopiperazine ring in addition to the isobutyl and naphthyl functional groups previously introduced and pendant to the first and second diketopiperazine rings respectively.

Figure 9:
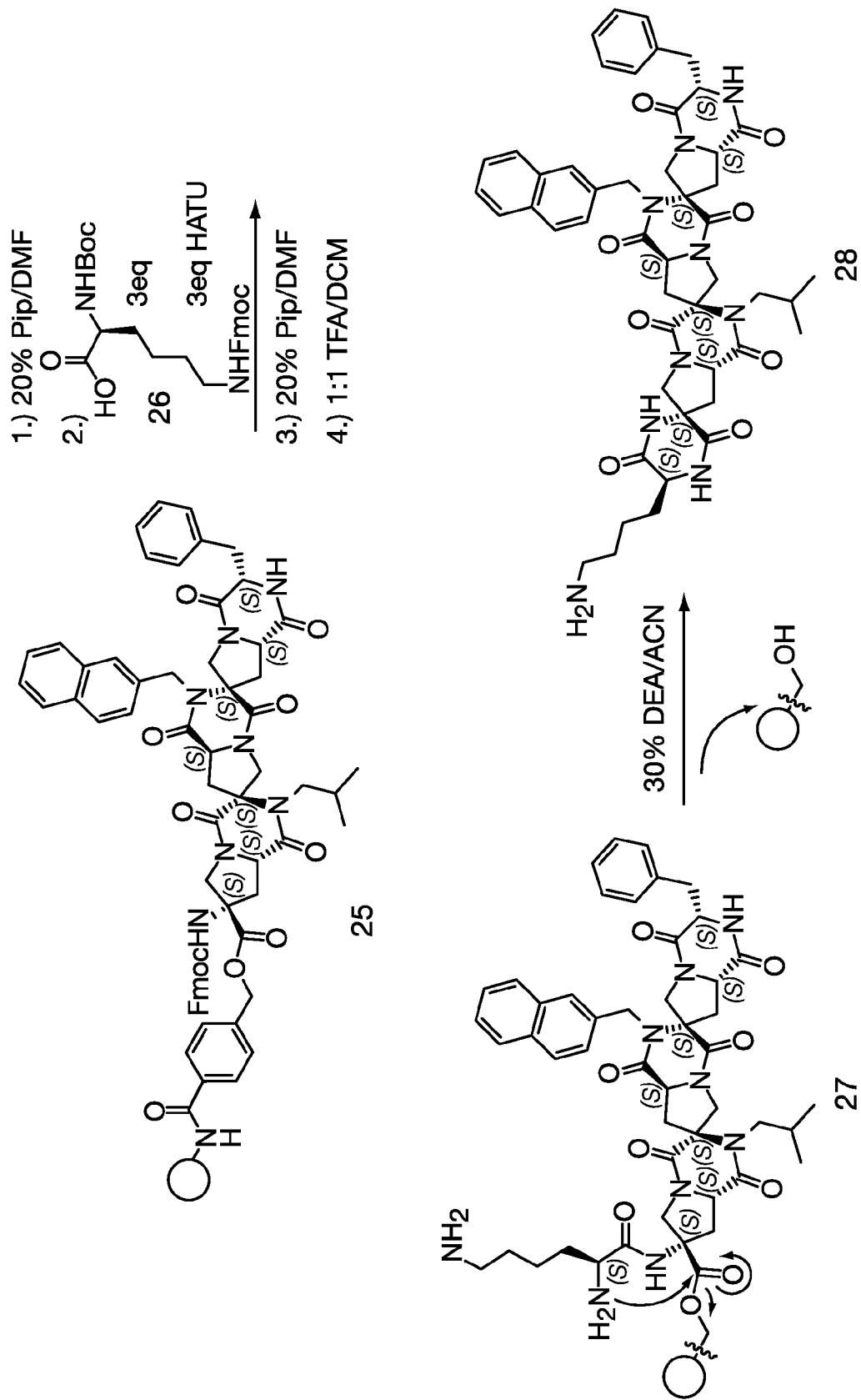
FIGS. 9-11 illustrate the further functionalization of the bis-peptide shown in FIG. 8.
Figure 10:
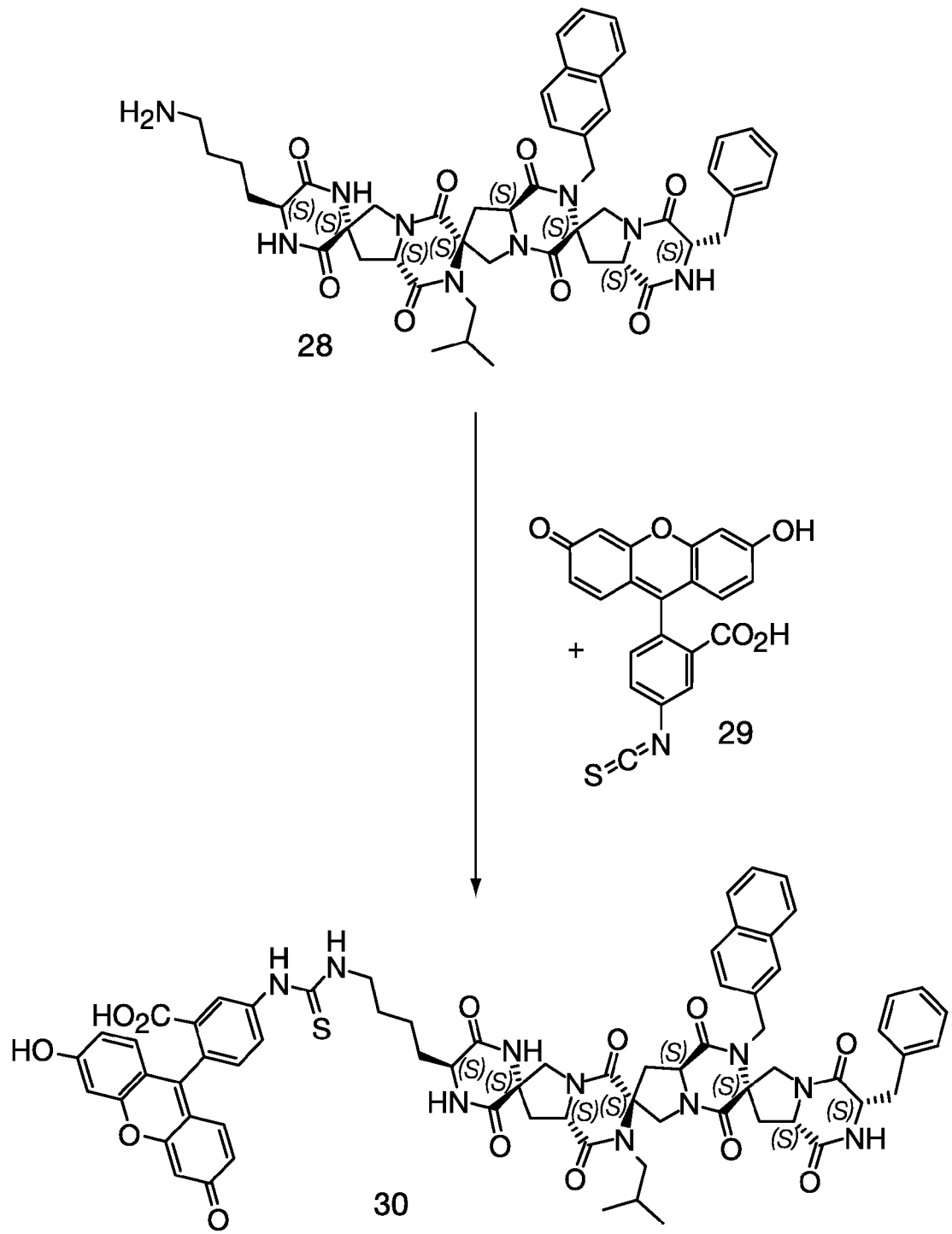

Bis-peptide 25 is reacted with 1) 20% Pip/DMF, 2) building block 26 and HATU (3 eq each), 3) 20% Pip/DMF, and 4) 1:1 TFA/DCM to produce bis-peptide 27 (FIG. 9). An aminobutyl-functionalized diketopiperazine ring is introduced at the terminus of the bis-peptide molecule and release from the HMBA resin is accomplished by treating bis-peptide 25 with 30% DEA/ACN, thereby obtaining functionalized free bis-peptide 28. As shown in FIG. 10, the primary amine group in bis-peptide 28 is reacted with thiocyanate 29 (2 eq, together with 2 eq DIPEA in DMF) to yield bis-peptide 30, containing a fluorescent label (a fluorescein functional group) attached to the aminobutyl-functionalized terminus of the bis-peptide scaffold.

Figure 11:
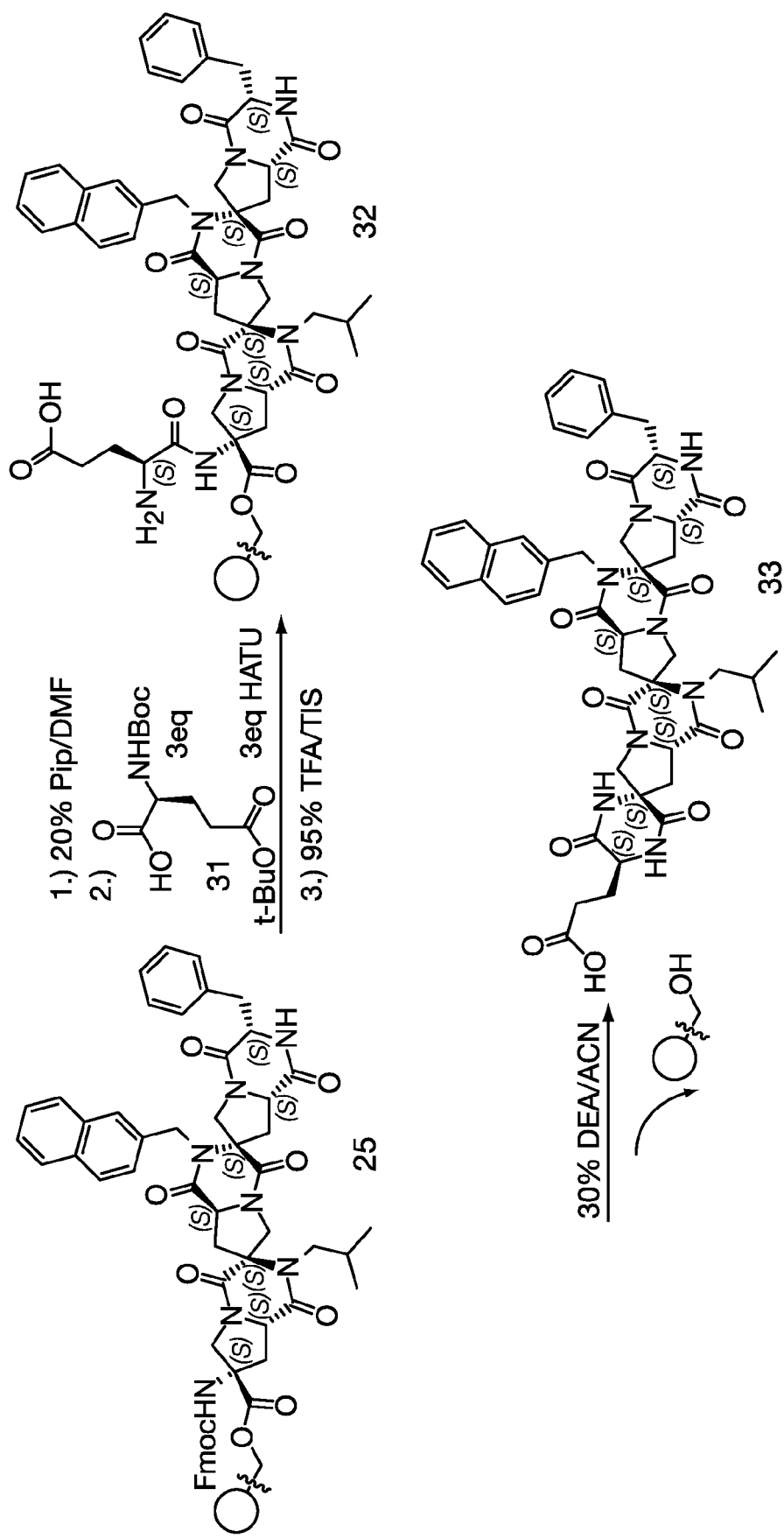

Alternatively, as shown in FIG. 11, a carboxylic acid-functionalized diketopiperazine ring is introduced by reacting bis-peptide 25 with 1) 20% Pip/DMF, 2) building block 31, 3) 95% TFA/TIS to obtain bis-peptide 32. Bis-peptide 32 is then treated with 30% DEA/ACN to release the bis-peptide from the resin, thereby yielding free bis-peptide 33. Bis-peptide 33 contains four diketopiperazine rings linked in a spiro manner by methylene groups as well as four pendant functional groups (HOC(=O)CH$_2$CH$_2$—, isobutyl, 2-naphthyl, and benzyl).

Example 15

Figure 12:
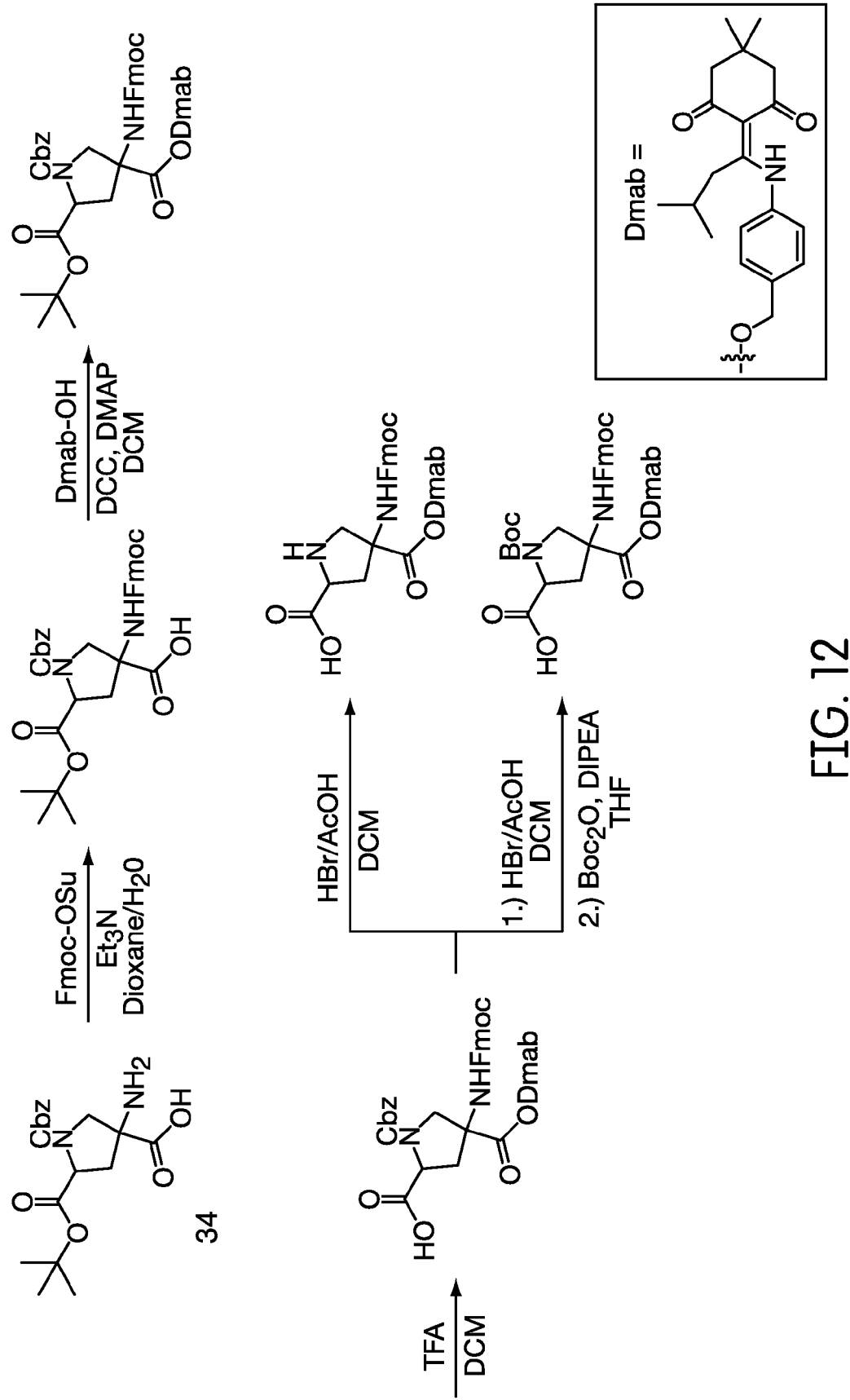
FIG. 12 illustrates the preparation of building blocks useful in the practice of the invention.

FIG. 12 illustrates the preparation of various building blocks useful in the practice of the present invention. Starting material 34 may be obtained from trans-4-hydroxy-L-proline using the procedures described in Levins et al., J. Am. Chem. Soc., Vol. 124, 2003, pp. 4702-4703 and Schafmeister et al., Accts. Chem. Res., Vol. 41, No. 10, October 2008, pp. 1387-1398.

Figure 13:
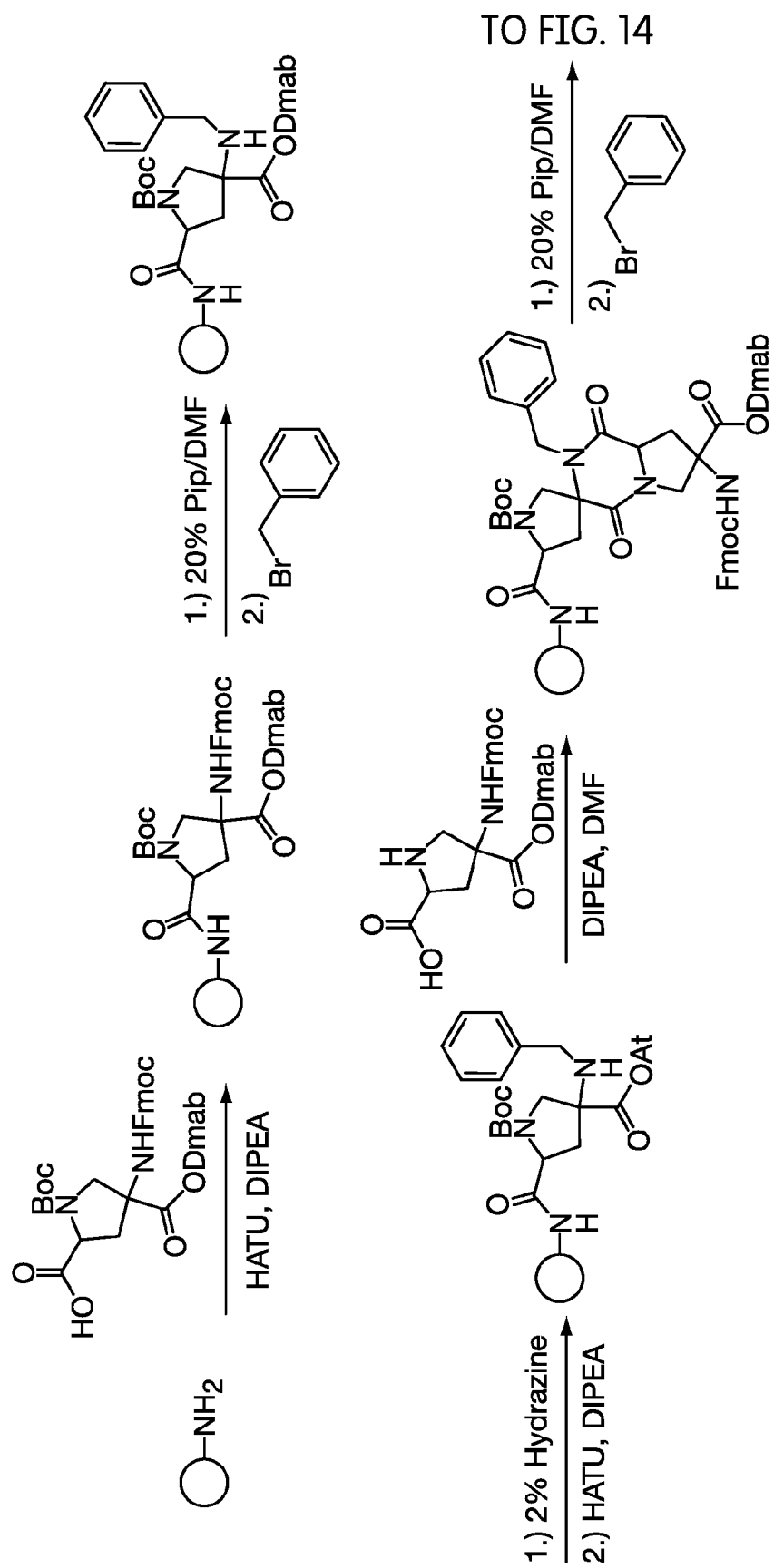
FIGS. 13 and 14 illustrate the on-resin assembly and functionalization of the building blocks of FIG. 12 to provide a functionalized bis-peptide.
Figure 14:
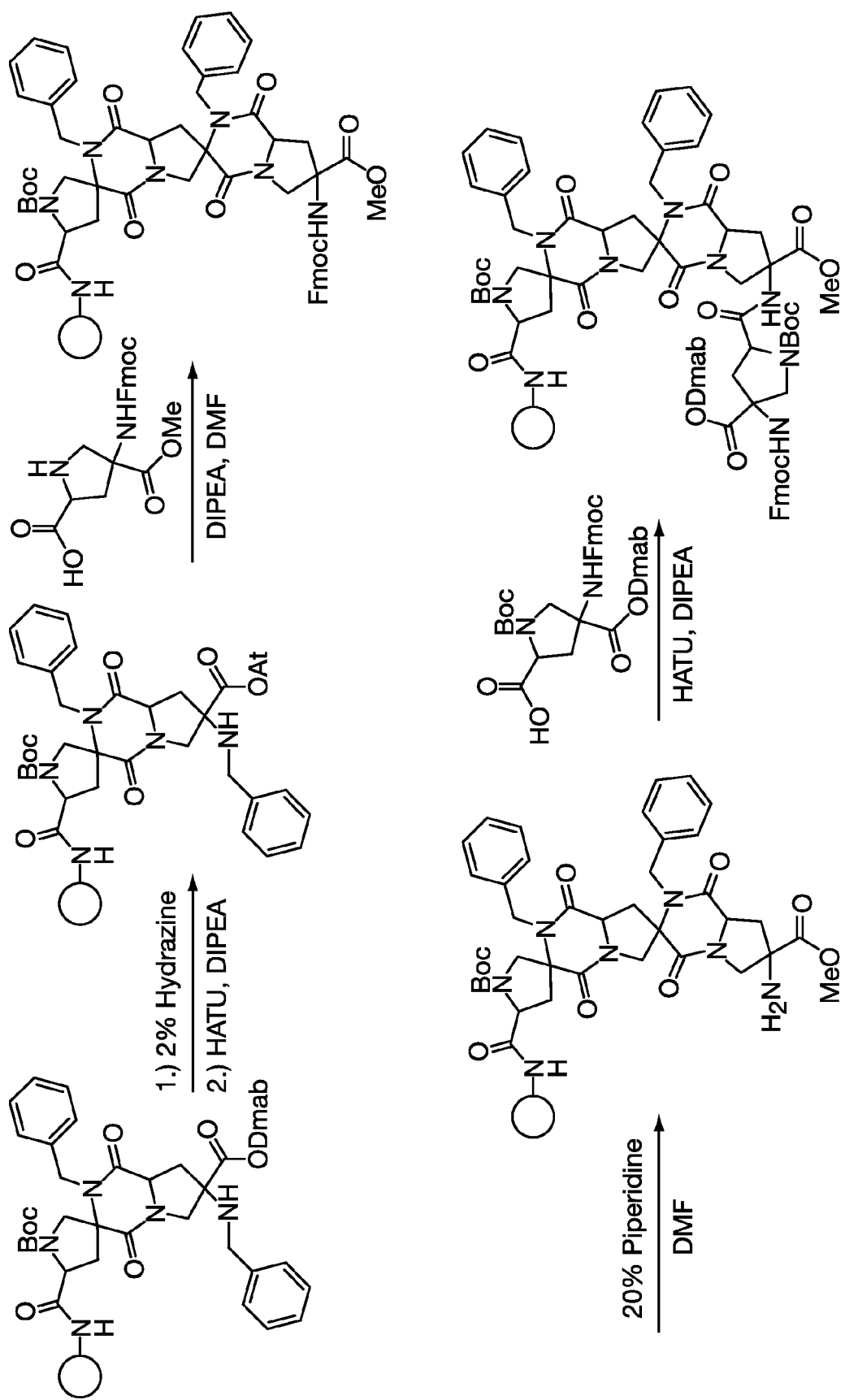

FIGS. 13 and 14 show how the protected amine groups of such building blocks can be functionalized during a solid state synthesis of a bispeptide oligomer (the submonomer approach). The introduction of benzyl functional groups by a halide displacement reaction is specifically illustrated in FIGS. 13 and 14, but other functional groups may also be introduced using similar techniques (e.g., through reaction with other halo-substituted hydrocarbons). Other reactions such as reductive amination (using a aldehyde or ketone) may also be utilized as methods of attaching various functional groups to a nitrogen atom of the building block once it has been incorporated into the bis-peptide.

Example 16

Figure 15:
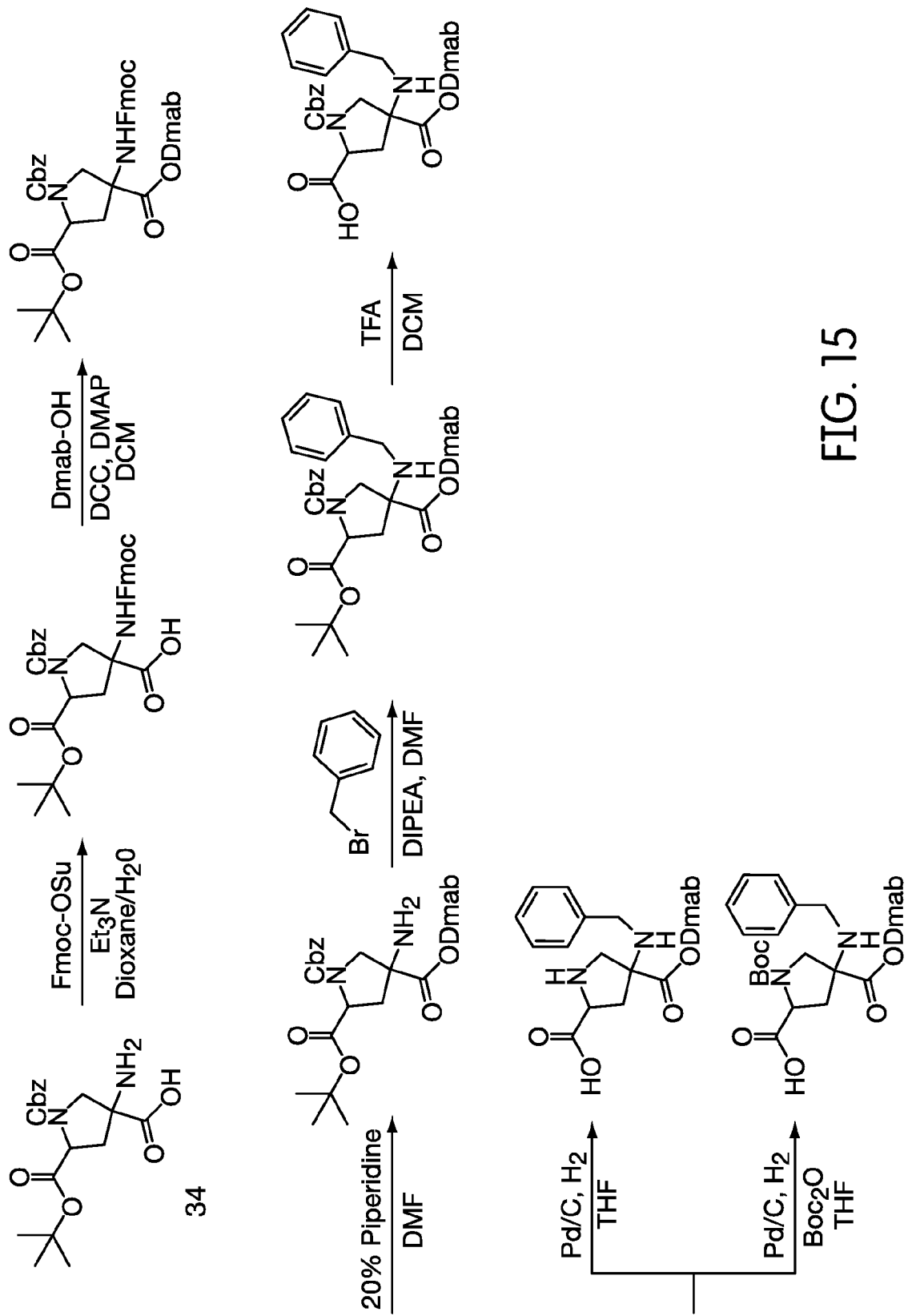
FIG. 15 illustrates the synthesis of functionalized building blocks useful in the invention.

FIG. 15 illustrates the preparation of other building blocks useful in the practice of the present, wherein such building blocks are pre-functionalized (i.e., the functional group is attached to a nitrogen atom of the building block before the building block is reacted to form a bis-peptide). The introduction of a benzyl functional group by a halide displacement reaction is specifically illustrated in FIG. 15, but other functional groups may also be introduced using similar techniques. Other reactions such as reductive amination may also be utilized as methods of attaching various functional groups to a nitrogen atom of the building block.

Figure 16:
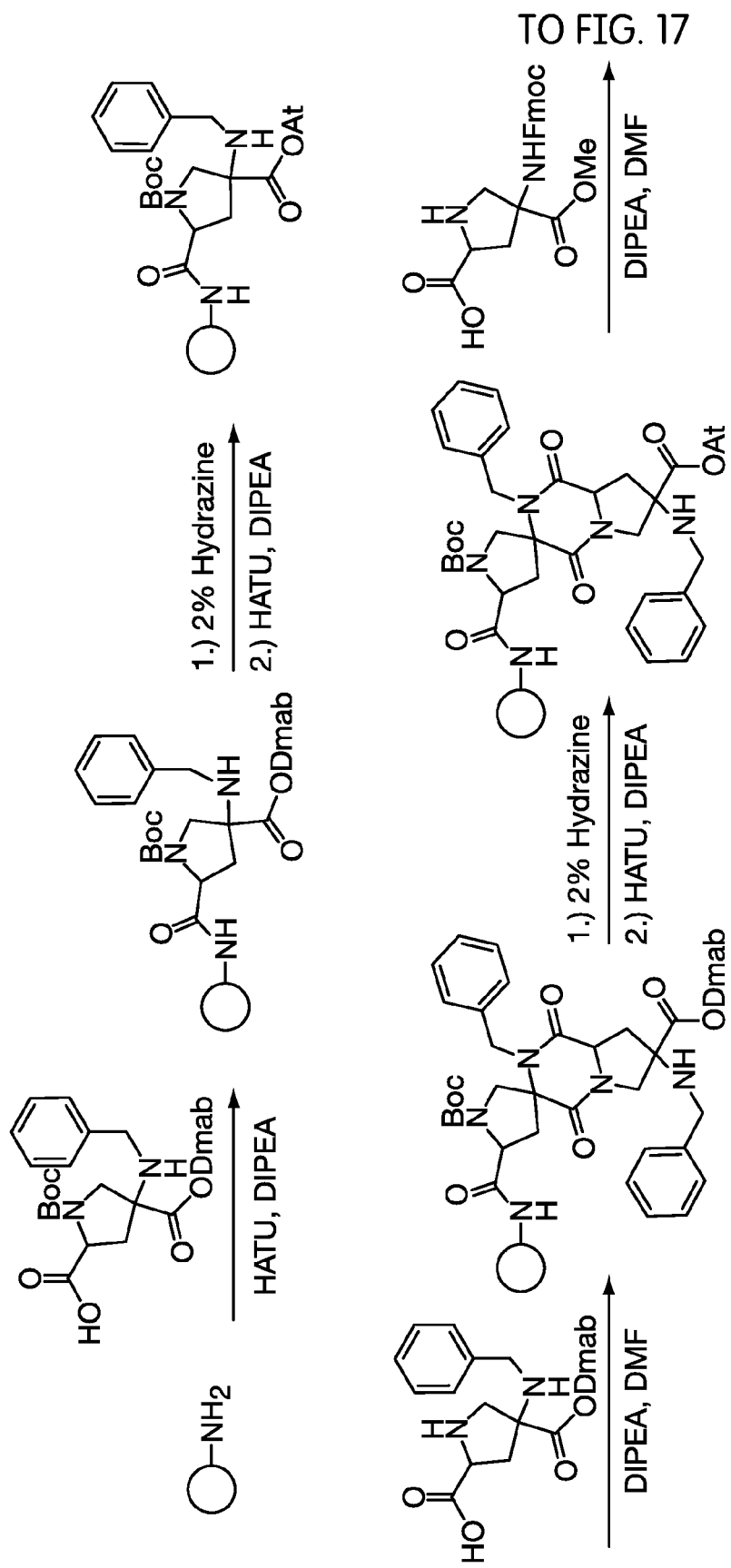
FIGS. 16 and 17 illustrate the on-resin assembly of the functionalized building blocks of FIG. 15 to provide a functionalized bis-peptide.
Figure 17:
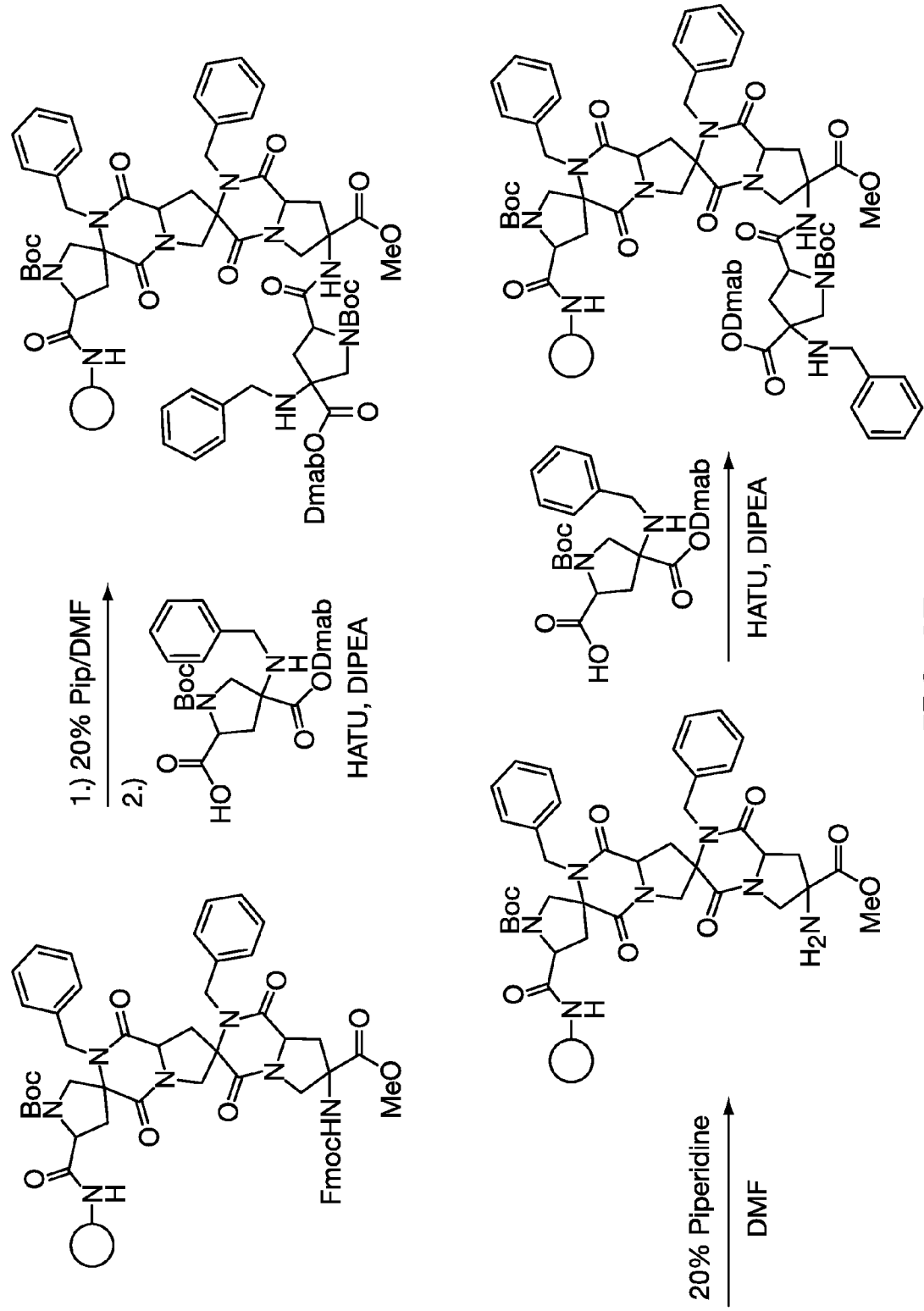

FIGS. 16 and 17 show how such pre-functionalized building blocks can be assembled into a bis-peptide oligomer using a solid state synthesis approach. If so desired, the assembled bis-peptide may be released from the resin once the synthesis is completed.

Example 17

This example demonstrates the preparation of functionalized bis-peptides in accordance with the invention that mimic the HDM2-bound conformation of the p53 activation domain. Two series of bis-peptides were synthesized, one of structural analogs and one of stereochemical analogs, to give entry 1 (Table 4), that binds HDM2 at 400 nM, penetrates human liver cancer cells through passive diffusion and suppresses the levels of p53 in a dose-dependent manner. This is the opposite biological effect of nutlin-3a, MI-219 and artificial oligomers that have been developed to bind HDM2. In a liver cancer cell line with mutant p53, entry 1 increases the levels of HDM2 up to 33-fold in a dose-dependent manner. Without wishing to be bound by theory, it is believed that entry 1 stabilizes HDM2 to proteolysis and that its moderate affinity for HDM2 allows the elevated levels of HDM2 to ubiquitinate p53, targeting it for proteolytic degradation. The suppression of p53 by compounds such as entry 1 could find application to temporarily curb p53-mediated apoptosis in cancer radio- and chemo-therapy and could serve as a chemical probe for effects of p53 suppression.

To identify functionalized bis-peptides that could mimic the HDM2 bound conformation of p53, an in-house developed software package called CANDO (see Schafmeister et al., *Acc. Chem. Res.* 2008, 41, 1387-1398) was used that builds millions of bis-peptides, varying back-bone stereochemistry and conformations as well as side-chain conformations to identify bis-peptides that could present functional groups to mimic the presentation of the Ca-Cp bond vectors of residues Phe19, Trp23 and Leu26 of p53 bound to HDM2 from the X-ray crystal structure. CANDO presented several stereoisomers out of 256 possible (eight stereocenters) that modeling suggested could mimic p53 including the stereoisomer with all (S) stereochemistry. Entries 1 and 3-12 were then synthesized on solid support to provide two series of bis-peptides which explore the effects of both functional groups and stereochemistry on the binding to HDM2.

To measure the binding affinity of functionalized bispeptides to HDM2, a direct binding fluorescence polarization assay was utilized. The binding of the fluorescein labeled bispeptides was measured at 10 nM in the presence of varying concentrations of $HDM2_{25-117}$. See Zondlo et al. *Biochemistry* 2006, 45, 11945-11957. Under the conditions of this assay, a fluoresceinated derivative of the p53 peptide (at 10 nM) had a measured $K_d$ of 0.62 μM, in close agreement with previously published results. The initial screen of bis-peptides including entries 3-7 was carried out on the bis-peptide backbone containing all (S) stereochemistry to identify appropriate functional groups to mimic the side chains of Phe19, Trp23 and Leu26 of the p53 helix. A representative subset of the bispeptides in this side-chain screen is shown in Table 3. Changing either $R_1$ or $R_3$, the surrogates for the side chains of phenylalanine and leucine, had little effect on the binding of the bis-peptides. However, using different substituted aromatic functional groups ($R_2$) in place of tryptophan showed an 8-fold improvement in binding by using the dichlorobenzyl group (bis-peptide entry 7) in place of the natural indole ring.

TABLE 3

| Entry | $R_1$ | $R_2$ | $R_3$ | Kd (μM) |
|---|---|---|---|---|
| 3 | benzyl | 2-naphthylmethyl | isobutyl | 46.0 |
| 4 | benzyl | 5-chloroindol-3-ylmethyl | isobutyl | 14.0 |
| 5 | benzyl | 3,4-dichlorobenzyl | isobutyl | 6.3 |
| 6 | 2-naphthylmethyl | 3,4-dichlorobenzyl | isobutyl | 6.5 |
| 7 | phenethyl | 3,4-dichlorophenethyl | isobutyl | 5.9 |

A second round of optimization was then undertaken by changing the stereochemistry of the bis-peptide scaffold to the other stereoisomers suggested by CANDO while keeping the side-chains the same (Table 4). Examination of the table shows an approximately 60-fold decrease in $K_d$ was achieved by tuning the presentation of the three side chains by changing the stereochemistry of the bis-peptide backbone. Entry 1, the tightest binding bis-peptide identified, had a $K_d$ of 0.4 µM, and bound more tightly than the fluoresceinated derivative of p53 ($^{Fl}$p53$_{14-29}$). Noteworthy in this stereochemical series of bis-peptides is the subtle relationship between stereochemistry and affinity. For example, entries 12 and 1 are epimers, with only a minor change in their relative orientation of their side chains by modeling, but they have a four-fold difference in binding. In contrast, the epimeric scaffolds 10 and 11 have nearly identical affinity for HDM2. Finally, bis-peptides 9 and 1 change only the stereocenter of the lysine residue to which the fluorophore is attached and display a nearly 17-fold increase in affinity. Modeling suggests that stereoisomer 1 projects the fluorescein side chain toward the protein surface while entry 9 projects it away, albeit far from the hydrophobic cleft normally associated with the binding of p53 to HDM2.

(human hepatocytic cells) for 24 hours at a concentration of 2 µM and observed with fluorescence microscopy (including confocal imaging), after washing away the media containing the fluorescein labeled bis-peptide. Significant uptake of entry 3 was seen as judged by the amount and fluorescent intensity of the cells, including distribution throughout the cytoplasm and nucleus as seen with confocal microscopy. Bis-peptide 1 was then incubated with both Huh7 cells and HepG2 (human liver hepatoblastoma cells) and imaged. Fluorescent images verified the distribution of entry 1 throughout the cytoplasm and nucleus. With this evidence of cellular uptake of fluorescently labeled bis-peptides, a determination of whether the uptake was through passive diffusion or active transport was sought. HepG2 cells were pre-cooled for 30 min at 4° C. in 475 µL of media and then 25 µL, of bis-peptide 1 in phosphate buffered saline (pH 7.4) was added to the media to achieve a concentration of 5 µM of entry 1. The cells were then incubated at 4° C. for 3.75 hours and then the media with entry 1 was removed. Fluorescence imaging showed substantial uptake of fluorescence that was indistinguishable from control cells treated with entry 1 at 37° C. In further experiments, HepG2 cells at 37° C. were pre-treated

TABLE 4

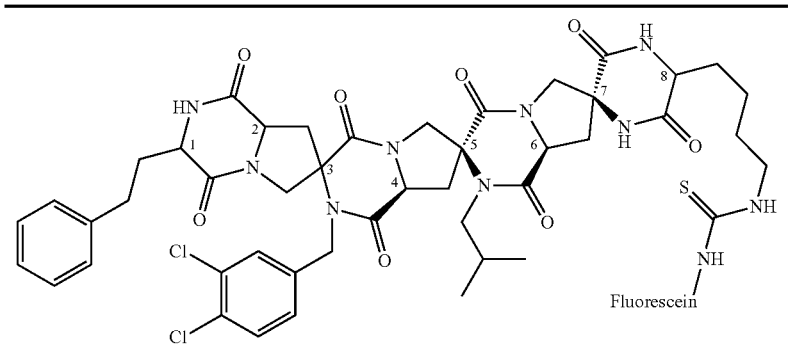

| Entry | \multicolumn{8}{c}{Stereocenter} | MDM2 |
|---|---|---|---|---|---|---|---|---|---|
|  | 1 | 2 | 3 | 4 | 5 | 6 | 7 | 8 | Kd (µM) |
| 8 | R | S | R | S | S | S | S | S | 23 |
| 9 | S | R | S | S | S | S | S | S | 6.7 |
| 10 | R | R | R | S | S | S | S | R | 4.8 |
| 11 | R | S | R | S | S | S | S | R | 4.6 |
| 12 | S | S | S | S | S | S | S | R | 1.6 |
| $^{Fl}$p53$_{14-29}$ | — | — | — | — | — | — | — | — | 0.62 |
| 1 | S | R | S | S | S | S | S | R | 0.4 |

To provide evidence that bis-peptides were binding into the hydrophobic cleft of HDM2, competition experiments were undertaken with a low nanomolar binding fluoresceinated mutant of the p53 peptide called $^{Fl}$p4 ($K_d$ is 0.16 µM for HDM2). Incubating $^{Fl}$p4 at 10 nM with 2 µM HDM2 and a series of varying concentrations of a bis-peptide which lacked the fluorescein group gave a $K_i$ of 5 µM. These results suggest that the bis-peptide lacking a fluorescein was able to compete with a fluorescein labeled p53-analog that is known to bind to the hydrophobic groove of HDM2. Finally, to demonstrate the selectivity of bis-peptide entry 1, binding experiments with HDMX, a homolog of HDM2, were undertaken. Entry 1 had a measured $K_d$ of 19 µM, demonstrating that it is selective for HDM2.

The effect of the sub-micromolar HDM2 binding bis-peptide 1 in cell-culture was thereafter evaluated. The cell-penetrating capability of two of the functionalized bis-peptides was first examined. Entry 3 was incubated with Huh7 cells with 10 mM sodium azide together with 50 mM deoxy-D-glucose (60 minutes pre-treatment) followed by addition of entry 1; these also showed uptake of fluorescence at levels that were indistinguishable from control cells treated with entry 1 at 37° C. Incubation of both cell lines with fluorescein at 37° C. as a control produced no visible uptake of fluorescence. Despite having molecular weights in excess of 1,300 Daltons, both entry 1 and entry 3 penetrate human cells and entry 1 penetrates cells in a manner consistent with passive diffusion. The lack of flexibility and the fact that five of the eight amides of these compounds are N-alkylated may contribute to their good bioavailability despite their large size.

To assess the biological effect of bis-peptide 1 in human cell culture, we carried out a series of western blot analyses using HepG2 cells, which express wild-type p53 and HDM2. HepG2 cells were incubated with bis-peptide 1 in media at 2, 5, 10 and 20 µM for 17 hours at 37° C. Western blot analysis showed the surprising result that p53 levels dropped up to 2.9-fold in a dose-dependent manner. An increase in p53 levels is seen with nutlin-3a and other HDM2 ligands. Also surprising was that HDM2 levels increased up to 4-fold as the concentration of entry 1 increased. Huh7 cells have a Y220P mutation that prevents HDM2 degradation of p53. Huh7 cells were incubated with bis-peptide 1 under the conditions described above for HepG2 and western blot analysis showed a dose dependent increase of HDM2 levels up to 33-fold relative to control cells. Quantitative real-time PCR analysis of Huh7 cells treated with bis-peptide 1 showed no effect of 1 on the level of mRNA for HDM2. Without wishing to be bound by theory, it is believed that entry 1 somehow stabilizes HDM2 to proteolysis and, because it is not an extremely tight ligand of HDM2, the increased levels of HDM2 lead to more ubiquitination and degradation of p53 in the wt-p53 HepG2 cells the level of mRNA for HDM2. A possible hypothesis is that entry 1 somehow stabilizes HDM2 to proteolysis and, because it is not an extremely tight ligand of HDM2, the increased levels of HDM2 lead to more ubiquitination and degradation of p53 in the wt-p53 HepG2 cells.

Thus, a series of functionalized bis-peptides were synthesized that screened side-chain compatability and backbone stereochemistry to mimic the conformation of p53 bound to HDM2. A bis-peptide (entry 1 in Table 4) was developed that binds HDM2, penetrates human cells by passive diffusion and has the effect of stabilizing HDM2 and suppressing p53 in cell culture. These results suggest that bis-peptides in accordance with the present invention, despite their size, can have good drug properties and can be developed to bind protein surfaces.

Example 18

To illustrate the ability to rapidly synthesize diketopiperazine based bis-peptide oligomers in accordance with the present invention, a homologous series of functionalized bis-peptides was synthesized using the following general procedures.

General Procedure A for MSNT Loading of the HMBA Resin

The solid-phase syntheses were carried out in polypropylene, open, fritted solid-phase extraction vessels with an attached bottom valve that allows the resin to be drained under vacuum. The resin was pre-swollen in DCM for 30 minutes. Initial loading of the benzylhydroxyl group of HMBA resin (16, FIG. 8) (75 mg of HMBA resin, 0.88 mmole/gm) was accomplished by combining 3 equivalents of Fmoc acid derivative 17 (FIG. 8), 3 equivalents of MSNT and 2.25 equivalents of MeIM in DCM at 200 mM concentration of 17. The solution was allowed to mix with the resin using magnetic stirring for 1 hour, followed by thorough washing of the resin three times (1 minute each) with DCM. The loading esterification was then repeated using the same procedure to ensure quantitative loading of the resin.

General Procedure B for Removal of the Boc and tert-Butyl Groups

To simultaneously remove the prolinyl amino acid Boc and tert-Butyl ester protecting groups of the resin bound oligomer, 95% trifluoroacetic acid was used in the presence of 5% triisopropylsilane as a cationic scavenger. 2 mL total of the solution was used per 100 mg of resin. Two TFA treatments were used for one hour each, followed by thorough washing of the resin. The resin was then treated with 5% DIPEA in DMF (1 mL) for 5 minutes to neutralize TFA salts and then washed three times with DCM (1 minute each).

General Procedure C for HBr Deprotection of Cbz and tert-butyl ester Groups

To simultaneously remove the prolinyl amino acid Cbz and tert-Butyl ester protecting groups of the resin bound oligomer, the resin was treated with a solution composed of 1 mL of DCM together with 1 mL of HBr (33% in AcOH) for 20 minutes. The treatment was repeated one additional time. The resin was then washed (3×DCM, 1 minute each) and then treated with 5% DIPEA in DMF (1 mL) for 5 minutes to neutralize salts. The resin was then washed (3×DCM, 1 minute each).

General Procedure D for Bis-amino Acid Activation

The bis-amino acid to be activated (3 eq relative to resin loading) and HOAT (6 eq relative to bis-amino acid) were dissolved in 1:2 DMF/DCM (concentration of 55 mM of bis-amino acid) with stirring. DIC (1 eq relative to bis-amino acid) was then added and the activation was allowed to proceed for 1.5 hours. This solution was then used immediately for each coupling step.

General Procedure E for Bis-amino Acid Coupling

The resin was suspended in DMF (~300 μL), DIPEA (2 eq relative to resin loading) was added and the solution containing the activated bis-amino acid (see General Procedure D) was then added to the resin. The reaction was allowed to proceed at room temperature for 3 hours with stirring, after which time the resin was thoroughly washed (3×DCM, 1 minute each). The resin was then suspended in 1.5 mL of 1:1 DCM/DMF with 3 equivalents of HOAt (relative to resin loading) followed by an additional aliquot of DIC (3 eq relative to resin loading). The reaction was allowed to stir for 1 hour followed by thorough washing of the resin with DMF and DCM (3×DMF, 3×DCM, 1 minute each).

General Procedure F for Removal of Fmoc Group

Fmoc deprotection was conducted by treatment of the resin with 20% piperidine in DMF for 5 minutes, washing the resin five times with DMF (1 minute each), treatment with 20% piperidine in DMF for 15 minutes, and finally washing the resin five times with DMF (1 minute each).

General Procedure G for Coupling an Amino Acid

The Boc-protected amino acid (4 eq relative to resin loading) was dissolved in DMF (concentration of 200 mM) with HATU (1 eq relative to amino acid), followed by the addition of 2 eq (relative to amino acid) of DIPEA. The solution was allowed to preactivate for 10 min and then the activation solution was added to the resin. The reaction was allowed to proceed for 45 min, followed by thorough washing of the resin with DMF and DCM (3 times each, one minute each).

Preparation of Homologous Bis-Peptides

Figure 18:
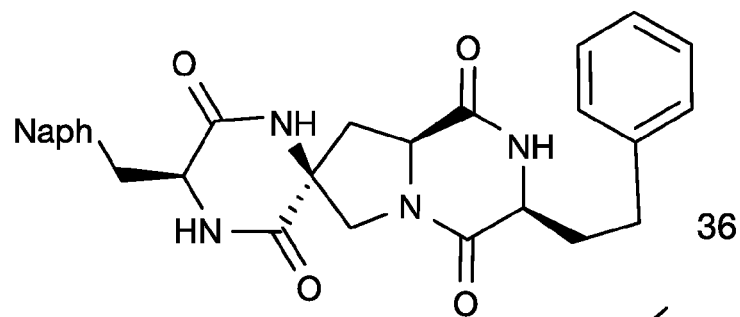
FIG. 18 shows a homologous series of functionalized bis-peptides in accordance with the invention.
Figure 18:
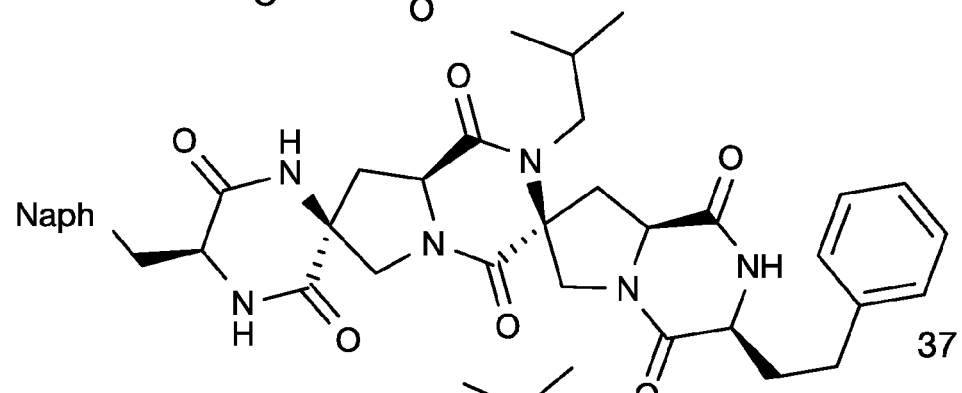
Figure 18:
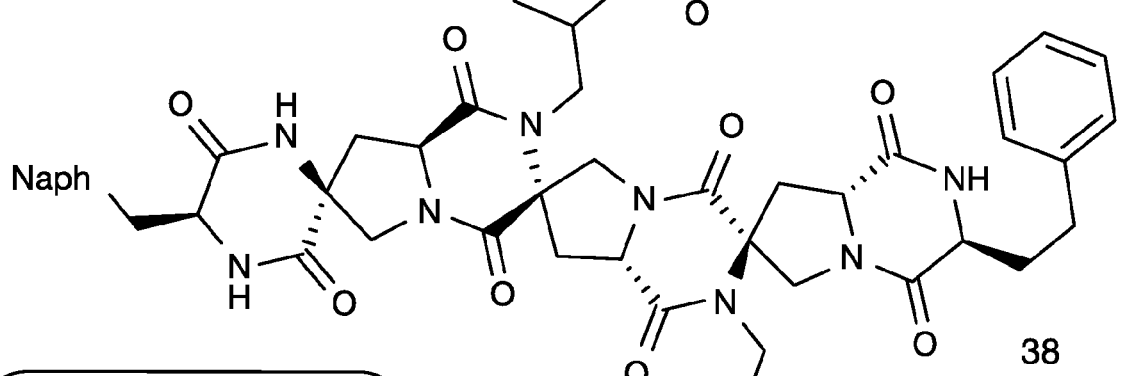
Figure 18:
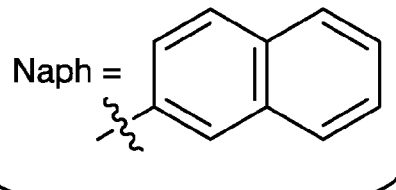
Figure 18:
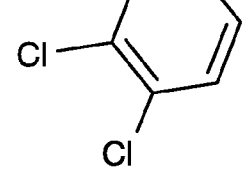

Starting with the HMBA resin, the Fmoc protected pro4 derivative 17 (FIG. 8) was loaded using the MSNT/MeIM protocol (Procedure A). Following treatment with 95% TFA to expose the prolinyl amino acid (Procedure B), the resin was split into approximately two equal portions. To the first portion, Boc-Homophenylalanine-OH was coupled (Procedure G), followed by deprotection and diketopiperazine closure. The Fmoc group was then removed, the primary amine was acylated with Boc-Naphthylalanine-OH (Procedure F, G), and then deprotected (Procedure B). Upon treatment of the resin with 10% DIPEA in DMF, diketopiperazine formation and spontaneous release from the resin was affected to give compound 36 (FIG. 18). To the other portion of the resin, an additional functionalized pro4 derivative 19 (FIG. 8), pro4(S, S, isobutyl functionalized) was coupled (Procedures D and E) and subsequently deprotected (Procedure B). The resin was again split into two portions; to one portion was coupled with the same residues as above (Homophenylalanine and Naphthylalanine, Procedure G) to give fully rigidified oligomer 37

(FIG. 18). To the other portion was coupled with an additional pro4 monomer, pro4(R,S, dichlorobenzyl) (Procedures D and E) and then coupled with homophenylalanine and naphthylalanine (Procedure G, B, F, G, B) on the termini of the oligomer as above to give rigidified pentamer 38 (FIG. 18). This homologous series is shown in FIG. 18 and illustrates the extensible, highly functionalizable nature of bis-peptides in accordance with the present invention.

What is claimed is:

1. A bis-peptide comprising a plurality of 2,5-diketopiperazine rings, wherein at least one 2,5-diketopiperazine ring contains a tertiary amide nitrogen atom bearing a pendant functional group, wherein the bis-peptide has a structure:

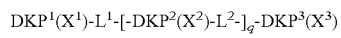

wherein q is 0 or an integer of from 1 to 50; $DKP^1$, $DKP^2$ and $DKP^3$ are 2,5-diketopiperazine rings; $X^1$, $X^2$ and $X^3$ are the same or different and are hydrogen or functional groups attached to an amide nitrogen atom of the 2,5-diketopiperazine ring, subject to the provisos that i) at least one of $X^1$, $X^2$ or $X^3$ is a pendant functional group which is not hydrogen and ii) when q is greater than 1, $X^2$ may differ among the -$DKP^2(X^2)$-$L^2$-repeating units; and $L^1$ and $L^2$ are the same or different and are linking moieties, subject to the proviso that when q is greater than 1, $L^2$ may differ among the -$DKP^2(X^2)$-$L^2$-repeating units;

the pendant functional group has a structure $CH(R^1)(R^2)$ and $R^1$ and $R^2$ are each independently selected from the group consisting of hydrogen, Ar, (C1-C6)-straight or branched alkyl, (C2-C6)-straight or branched alkenyl or alkynyl, (C5-C7)-cycloalkyl substituted (C1-C6)-straight or branched alkyl, (C5-C7)-cycloalkyl substituted (C3-C6)-straight or branched alkenyl or alkynyl, (C5-C7)-cycloalkenyl substituted (C1-C6)-straight or branched alkyl, (C5-C7)-cycloalkenyl substituted (C3-C6)-straight or branched alkenyl or alkynyl, Ar-substituted (C1-C6)-straight or branched alkyl, Ar-substituted (C3-C6)-straight or branched alkenyl or alkynyl; wherein any one of the $CH_2$ groups of said alkyl chains is optionally replaced by a heteroatom selected from the group consisting of O, S, SO, $SO_2$, and NR; wherein R is selected from the group consisting of hydrogen, (C1-C4)-straight or branched alkyl , (C3-C4)-straight or branched alkenyl or alkynyl, and (C1-C4) bridging alkyl wherein a bridge is formed between the nitrogen and a carbon atom of said heteroatom-containing chain to form a ring, and wherein said ring is optionally fused to an Ar group; wherein Ar is a carbocyclic aromatic group selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl , oxazolyl, thiazolyl, imidazolyl, pyraxolyl, 2-pyrazolinyl, gyrazolidinyl, isoxazolyl, isotriazolyl, 1,2,3-oxadiazolyl, 1,2,3-triazol 1,3,4-thiadiazol pyridazinyl, pyrimidinyl, pyrazinyl 1,3,5-triazinyl, 1,3,5-trithianyl, indolizinyl, indolyl, isoindolyl, 3H-indolyl, indolinyl, benzo[b]furanyl, benzo[b]thiophenyl 1H-indazol, benzimidazol benzthiazol purinyl, 4H-quinolizinyl, quinolinyl, 1,2,3,4-tetrahydroguinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl; wherein Ar is optionally substituted with one or more substituents which are independently selected from the group consisting of hydrogen, halogen, hydroxyl, nitro, —$SO_3H$, trifluoromethyl, trifluoromethoxy, (C1-C6)-straight or branched alkyl, (C2-C6)-straight or branched alkenyl, —O—[(C1-C6)-straight or branched alkyl], —O—[(C3-C4)-straight or branched alkenyl], —O-benzyl, —O-phenyl, 1,2-methylenedioxy, —$NR^5R^6$, carboxyl, —N—(C1-C5-straight or branched alkyl or C3-C5-straight or branched alkenyl) carboxamides, —N,N-di-(C1-C5-straight or branched alkyl or C3-C5-straight or branched alkenyl) carboxamides, morpholinyl, piperidinyl, —O-M, —$CH_2$—$(CH_2)_r$-M, —O—$(CH_2)_r$-M, —$(CH_2)_r$—O—M, and —CH=CH-M; wherein $R^5$ and $R^6$ are independently selected from the group consisting of hydrogen, (C1-C6)-straight or branched alkyl, (C3-C6)-straigdht or branched alkenyl or alkynyl and benzyl; wherein M is selected from the group consisting of 4-methoxyphenyl, 2-pyridyl, 3-pyridyl,4-pyridyl, pyrazyl, quinolyl, 3,5-dimethylisoxazoyl, 2-methylthiazoyl , thiazoyl, 2-thienyl, 3-thienyl and pyrimidyl; and r is 0-2; and each of $L^1$ and $L^2$ independently consists of i) two —$CH_2$— groups, ii) a —$CH_2$— and a —$CH_2CH_2$— group or iii) a tetravalent —$CH(CH_2$—$)$—$CH(CH_2$—$)(CH_2CH_2$—$)$ group, which are or is part of a ring structure which also includes an amide nitrogen and a carbon atom of one 2,5-diketopiperazine ring and a carbon atom of the adjacent 2,5-diketopiperazine ring.

2. The bis-peptide of claim 1, wherein the bis-peptide contains at least two different $CH(R^1)(R^2)$ groups.

3. A method of making a bis-peptide in accordance with claim 1, said method comprising reacting a first building block containing a first secondary amine group and a free carboxylic acid group alpha to the first secondary amine group with a second building block containing an activated acyl group that is more susceptible to nucleophilic attack by a secondary amine than a free carboxylic acid group or a methyl ester group, and a second secondary amine group alpha to the activated acyl group, wherein at least one of the first secondary amine group or the second secondary amine group bears a functional group corresponding to the pendant functional group having the structure $CH(R^1)(R^2)$.

4. The method of claim 3, wherein the first building block is immobilized on a resin which is an aminomethyl polystyrene resin and the bis-peptide remains covalently attached to the resin until cleaved from the resin.

5. The method of claim 3, wherein the second building block additionally contains a protected amine group having a protecting group selected from Cbz, Fmoc or t-Boc.

6. The method of claim 5, wherein the protected amine group is deprotected after formation of the bis-peptide by removing the protecting group to provide a reactive amine group that is reacted with a third building block containing a second activated acyl group and a third secondary amine group alpha to the second activated acyl group.

7. The method of claim 3, wherein the first secondary amine group is part of a five- or six membered nitrogen-containing heterocyclic ring.

8. The method of claim 3, wherein the first secondary amine group is obtained by deprotecting a protected amine group having a protective group selected from Cbz, Fmoc or t-Boc to form a primary amine group and functionalizing the primary amine group to provide the functional group by reductive amination involving reacting the primary amine group with an aldehyde or ketone or reaction of the primary amine group with a hydrocarbyl halide.

9. The bis-peptide of claim 1, wherein the pendant functional group is selected from the group consisting of phenyl, benzyl, p-cresol, 1-methoxy-benzene, naphthyl, imidazole, 4-methyl-phenol, 1-methoxy-4-methyl-benzene, 2-pyrene, 1-methylimidazole, indole, 2-pyridine, 3-pyridine, triazole, imidazole, ethanoic acid, acetic acid, propionoic acid, methyl formate, methyl acetate, ethanoamide, propionamide, carboxhydroxamide, ethanohydroxamide, propionhydroxamide, amine, methanamine, ethanamine, propanamine, N,N-dimethylmethanamine, methyl-guanidine, ethyl-guanidine, propyl-guanidine, dimethylamine, N,N,N-trimethylmethanamine, methylamine, methyl-thiourea, ethyl-thiourea, 1-(3, 5-bis(trifluoromethyl)phenyl)-3-ethylthiourea, 1-(3,5-bis(trifluoromethyl)phenyl)-3-ethylurea, methyl-azide, azide, isopropyl, isobutyl, isopentyl, ethyl, methyl, cyclopentyl, cyclohexyl, 1-methyl-propyl, hydroxyl, methyl-hydroxyl, thiol, methyl-thiol, methyl-ether, ethyl-ether, methyl-thioether, ethyl-thioether, ethene, allyl, ethyne, propargyl, guanine, adenine, cytosine, thymine, and fluorescein.

* * * * *